US006528303B1

(12) United States Patent
Herzog

(10) Patent No.: US 6,528,303 B1
(45) Date of Patent: Mar. 4, 2003

(54) NEUROPEPTIDE Y-Y5 RECEPTOR

(75) Inventor: Herbert Herzog, Bondi (AU)

(73) Assignee: Garvan Institute of Medical Research, New So. Wales (AU)

( * ) Notice: Subject to any disclaimer, the term of this patent is extended or adjusted under 35 U.S.C. 154(b) by 0 days.

(21) Appl. No.: 09/065,027

(22) PCT Filed: Nov. 8, 1996

(86) PCT No.: PCT/AU96/00706

§ 371 (c)(1),
(2), (4) Date: Apr. 22, 1998

(87) PCT Pub. No.: WO97/17440

PCT Pub. Date: May 15, 1997

(30) Foreign Application Priority Data

Nov. 9, 1995 (AT) .............................. PN 6467

(51) Int. Cl.$^7$ .......................... C12N 5/00; C12N 15/70; C12N 5/06; C12N 1/00; C07H 21/04
(52) U.S. Cl. .................... 435/325; 435/320.1; 435/348; 435/354; 435/358; 435/366; 435/369; 435/243; 435/252.1; 435/252.3; 536/23.5
(58) Field of Search ...................... 536/23.5; 435/320.1, 435/325; 800/13, 18

(56) References Cited

FOREIGN PATENT DOCUMENTS

| EP | 0 355 793 A2 | 2/1990 |
|---|---|---|
| WO | WO 93/09227 A1 | 5/1993 |
| WO | WO 96/16542 A1 | 6/1996 |
| WO | WO 96/16542 | 6/1996 |
| WO | WO 96/23809 | 8/1996 |
| WO | WO 96/23809 A1 | 8/1996 |
| WO | WO 97/20822 A1 | 6/1997 |
| WO | WO 97/37998 A2 | 10/1997 |
| WO | WO 97/46250 A1 | 12/1997 |

OTHER PUBLICATIONS

R. J. Wall, Transgenic Livestock: Progress and Prospects for the Future, 1996, Theriogenology, vol. 45 pp. 57–68.*
Hammer et al., Spontaneous inflammatory disease in transgenic rats expressing HLA–B27 and human B 2 m: An animal model of HLA–B27–Associated human disorders.*

Taurog et al., Cell surface expression and recognition as an alloantigen in the absence of human B2–microglobulin, Dec., 1988, J. Immunology, vol. 141 pp. 4020–4023.*
Mullins et al., Fulminant hypertension in transgenic rats harbouring the mouse Ren–2 gene, Apr.,1990, Nature, vol. 344 pp. 541–544.*
Mullins et al., Expression of the DBA/2J Ren–2 gene in the adrenal gland of transgenic mice, 1989, EMBO Journal, vol. 8 No. 13 pp. 4065–4072.*
Gehlert. (1994). "Subtypes of receptors for neuropeptide Y:Implications for the targeting of therapeutics," *Life Sci.* 55(8):551–562.
Gerald et al. (Jul. 11, 1996). "A receptor subtype involved in neuropeptide–Y–induced food intake," *Nature* 382:168–171.
Hu et al. (Oct. 18, 1996). "Identification of a novel hypothalamic neuropeptide Y receptor associated with feeding behavior," *J. Biol. Chem.* 271:26315–26319.
Matsumoto et al. (Nov. 1, 1996), "Inactivation of a novel neuropeptide Y/peptide YY receptor gene in primate species," *J. Biol. Chem.* 271(44):27217–27220.
Wahlestedt et al. (1993). "Neuropeptide Y–related peptides and their receptors–Are the receptors potential therapeutic drug targets?" *Ann. Rev. Pharmacol. & Toxicol.* 32:309–352.
Weinberg et al. (Jul. 12, 1996). "Cloning and expression of a novel neuropeptide Y receptor," *J. Biol. Chem.* 271:16435–16438.
Ball, H. J. et al., "Multiple Promoters regulate Tissue–specific Expression of the Human NPY–Y1 Receptor Gene" *J. Biol. Chem.,* 1995, 270:27272–27276.
Sambrook, J. et al., *Molecule Cloning (A Laboratory Manual),* 2nd Ed., (Cold Spring Harbor Laboratory Press, Cold Spring Harbor, New York), 1992.

* cited by examiner

*Primary Examiner*—Anne-Marie Baker
(74) *Attorney, Agent, or Firm*—Morrison & Foerster LLP

(57) ABSTRACT

The invention provides isolated DNA molecules encoding the human, mouse and rat NPY-Y5 receptors. These isolated DNA molecules can be used to express the NPY-Y5 receptors in cells which can then be used to screen compounds for NPY agonist and antagonist activity.

16 Claims, 26 Drawing Sheets

Figure 1

SEQUENCE RANGE : 1 to 8371

```
                                                                    70
        *         *         *         *         *         *         *
CTGCAGCGGCCGGGGCGCCCCGAGGTACGGGCTCCCGCCCCTCCCTGCCAACCCCTTTCGCGCCGGGTAG
                                                                   140
        *         *         *         *         *         *         *
GCCTGCACCGAGGGGCCGTGGCGGGTCCCCGCGCGGGCTGCGAGTCTGCGCAGGTCCCTGGGAGCCCGCA
                                                                   210
        *         *         *         *         *         *         *
CCCGTCTCTGGTGCCAGGGCGTTGTCGGGGGTCCCAAGAGAGCGGGGTGGGGAAGGTGAAGGGAGCGCGG
                                                                   280
        *         *         *         *         *         *         *
CTGGAAAAATGGGGATTAGGGTGGCGGAACAGGCACTTGTCAGGAGTGAAGAGACAGCGGAGAGGGTACT
                                                                   350
        *         *         *         *         *         *         *
GGGCTGAATTCTTTCGTGCCGAGCAGGTCCCTCCGGTTCCCAACTCACCCGGGTGGAGCAGGCGCGGGCC
                                                                   420
        *         *         *         *         *         *         *
GAACCCGGGAGGAGAGTGTCGGGGATCCGCGAAGGAGCCTCCTGGGGATGGGGCGGGGGATGGACAAAGC
                                                                   490
        *         *         *         *         *         *         *
GCTGCCCCGGCTGGACACGCTCTGGCGCTAGCCCGGCTGGCATCCGGAGCTGGGAACAGCAGCCCGCGG
                                                                   560
        *         *         *         *         *         *         *
GGTGCCCGGGTCAGGGCTCAACCTAGCGGGTCTCTGGCGAGGCCGGGGGCGCAGCCCGCGGGGCGCCACT
                                                                   630
        *         *         *         *         *         *         *
CAGGCCGTCCAGCTGCCGCGCGGTCCAGCGCTGACCCGAGCCCGGGAGGCAGCTGCGCTCTAAGGTTTGC
                                                                   700
        *         *         *         *         *         *         *
GCTCCTGTTTGCGAGGTGTCTTCATATAACAAATGCGAGCAATAACAAACATCCATAGAACTCGAATTCC
                                                                   770
        *         *         *         *         *         *         *
AGAAACGGGAATTCTTTTTTCCAAGTTCACAGACCTTTAGTTAATCTTTTAAAGGAACTGAGGCGTTGTG
                                                                   840
        *         *         *         *         *         *         *
TTGGACCAAAGCCAAAACGATTTTACCTTACACCATGGAAAATAGCCTAAGGCTCTTTTCAGCAGAATTT
```

Figure 1 Cont.

```
                                                                    910
         *         *         *         *         *         *         *
TTGGCAGTCCGAATGCAATTTTTAGATTTCAGATTTCTCAAGGGAAGAGAAACTCTGCTGTTAGAATTTG
                                                                    980
         *         *         *         *         *         *         *
GAAGGGAGGGTGGTGCATGCCTGTGTGTTTGTCAGCTGAGCAGAGCTGTATTTATCTTTCCAATTCAAAT
                                                                   1050
         *         *         *         *         *         *         *
TGTGCCAGATTCTGGCTTTAAGAAAAAACCATGGGAATATTTGAGAACATGGAATCATGCTGCTGTTCCA
                                                                   1120
         *         *         *         *         *         *         *
CGATCACAGCAAAACAGACAATAGTTGATATTGTATCATTGCAGGAGGAAAAAGAATTACATATATTTTA
                                                                   1190
         *         *         *         *         *         *         *
TTCTTTTGTGTGATTGTCATCCTTTGTGAAAAGAATGATGTGTATTTTCATAAAGCAAAAAATTATTCAA
                                                                   1260
         *         *         *         *         *         *         *
ACAAAGAAACCTTATTTAAATGTACAAGTCAGACTTTTAATATCCTTTGAATTCCCTGCAGTTCCTCCTA
                                                                   1330
         *         *         *         *         *         *         *
TTATTCTTGAGAACTATCTACTTGGTTAAAATACTTAAATCTATTCAGAAGGTTTCATTTGTCTAGGTGT
                                                                   1400
         *         *         *         *         *         *         *
CAGATATAGAAGAGTTTATAAGAAAATTCCAGTAAACCTTTAAAAAGATATTATTTTTTATAAGTTGCCA
                                                                   1470
         *         *         *         *         *         *         *
TAGTTTAATAAAGAACTTTTATTTTTCACACTTTTTACTCAGAGATTAAAGTTCTGTGTTTCAGCCTGGA
                                                                   1540
         *         *         *         *         *         *         *
AATTCTGATGGTGGGAGATACAACTAATACAAAAGAGAATGAGTAAATATAGTAATTAGGTATGACAAAA
                                                                   1610
         *         *         *         *         *         *         *
GTCTCATGCTGTCAATATCAGATTTCTTGTCAAATAATATTCCATGTTAAAATATTTTTTCTCTGGCTAT
                                                                   1680
         *         *         *         *         *         *         *
ATTTCATAATTTATATAGCAATTTCAGAAGATTCACATATATCATTACTTTTATAATAGATAAAATATGT
                                                                   1750
         *         *         *         *         *         *         *
TGCATAAAAATGACAGCACTCGTAATAACACTTGTTGAAATTTGGATTTCCATTGTAGGTCTGCTCATTG
```

Figure 1 Cont.

```
                *         *         *         *         *         *         *
                                                                          1820
TGTTTTCAGGAAAAAGGAAGGGAAAGGGTAAGTTTAATGGAAAAAATCCTGCTTTTTTGTTTGTTTTTC
                *         *         *         *         *         *         *
                                                                          1890
ATTTAAGTGCGTTCCTGTACCTTGAGTTTTCAAGTTAAATCTTATTGTACAAAATTTTCCTAATGTTTAA
                *         *         *         *         *         *         *
                                                                          1960
ACTAGGCCCTGGCTACCAGGAGGCACTTTTAAAAAAACTACACGTCCACCACCACCCCTCCCCCACCCGC
                *         *         *         *         *         *         *
                                                                          2030
CCTCCCTGCCTCCAGCATTTGCAATATTCATTATTTAGTTGTAAGAAGAAATTCTTCCTTCATTGGAGCA
                *         *         *         *         *         *         *
                                                                          2100
AAGATTCACAGAATGTTCATTCTGTGCAGACTATATATTAGATATTACATGTGTGTATGTTTATGTGGTA
                *         *         *         *         *         *         *
                                                                          2170
GATGGTGTGGGGTGGGGCTAGAGGGAGAGCAGGAGAAAGTTGACTACAGTCACACCAAAATAAAATGAAT
                *         *         *         *         *         *         *
                                                                          2240
AAATGAGTGTTGAATGAATCAAGTGCTAAGAGAGAATTTTTAAATTGCTTACCAATCTATCAGTAGCTAC
                *         *         *         *         *         *         *
                                                                          2310
ATAAGTATTCATTATATTCAGCAGTAATGCATGTGTCCATGCTATAGAGAAATAATATATTACTATCAGT
                *         *         *         *         *         *         *
                                                                          2380
CAGGAGAATGCCATTCATTTATTAATTCATTCATCATCCAATTTGGGCCTTTTTATATCTCAGCAATCTA
                *         *         *         *         *         *         *
                                                                          2450
CAGTTACTCAGGGTGTAGAGCTTGAATTAATCTATATAGAATATTCTTGGCATAGCACCTTGCATTAGTC
                *         *         *         *         *         *         *
                                                                          2520
GTCTTTATGCTTAGAGCAGAGCAGAGCACCTAGCAGAATATATGTTCAATAAATACTTTTTGAATGAATA
                *         *         *         *         *         *         *
                                                                          2590
AAAGAAGGAACAACTAATCATTCTTAGCTGTTCATTAATAGAAGGTGCCTACCCCTTTAAAATTATATAT
                *         *         *         *         *         *         *
                                                                          2660
AAATTATCTCTTTCTTAAAATACTCAAATGTTTTAAGGAATGAAAGAAGCATCCTCAGTTTTTTCTCCAG
```

Figure 1 Cont.

```
                                                              2730
     *         *         *         *         *         *        *
TGTCCAATGAATACTCAAGATGGCATTTATTTCATCTTCTTACTAAGGAGATGTGGTTTTACAATTTAAT
                                                              2800
     *         *         *         *         *         *        *
GCATTCAATATTTTATGTGCATATATTTAAAATAAAAGTTTTAATAACAGACTGCACAGTCGCGGAAATG
                                                              2870
     *         *         *         *         *         *        *
GATATACTTCTTTTTTCATTTACATTTTTAAATGTTGTAAATATATCTTACAGTTTTAGTTGCATGTTG
                                                              2940
     *         *         *         *         *         *        *
CTTGTGTGATAGCCTTTATCAATGAAGTTATCCAAATTTAAAGTGCTAAACTATCTTTATTGTCTGTCTA
                                                              3010
     *         *         *         *         *         *        *
GGTATCTCCTCCTCATTGCATTTTGGGGCCATTTGAAACATCTATAATTTCAATGGTTCTCTATAAATGT
                                                              3080
     *         *         *         *         *         *        *
ATATATAAAGATACATATACACACATATATATGTACACACAAAAATATAGTCATACTCTATCCTGAATTT
                                                              3150
     *         *         *         *         *         *        *
TCCCACATTGCCAGAATGATTCATTTCTGTTATTTTAAAGCAAGGGAAATTAAACTGCTTTTCTAAAACG
                                                              3220
     *         *         *         *         *         *        *
ATTGGTAAGAAATATTTACTTAGCATCCACTATGTGTAATATGCTTTATTAAACATCATTTCTAGAATGA
                                                              3290
     *         *         *         *         *         *        *
AAATAATTAAGAGTTTTATCTCCATTCGAATATAATAGAGAGGTCTAACCACATGGAATGGAGAAAAATC
                                                              3360
     *         *         *         *         *         *        *
TGAATTTTAGACTCAAAACTACATTGTTTCTATTACCACAAATTGTGCTGCATCTTCTCTTTCTTCAAAA
                                                              3430
     *         *         *         *         *         *        *
AATTTTGGACAGCAATTTTACACTAAGTAAGTATCATCCACAGTTACATGTTCCAAAAAGGCACAAAGCC
                                                              3500
     *         *         *         *         *         *        *
GTTGTAGAAGGGGCCATCTAATTTCTCTCTTGTTCTTGCTTAGGTGTTACAAGGAAAGGCTATCGGTAAC
                                                              3570
     *         *         *         *         *         *        *
AACTGACCTGCCACAAAGTTAGAAGAAAGGATTGATTCAAGAAAGTAAGTCAAGAGAAGAACAACTAAGC
```

Figure 1 Cont.

```
                *         *         *         *         *         *    3640
                                                                       *
AGGATTGCAGTTACAAGCAGCCTGTACACAATTATAAATATAAATAGGATCATGAATAAGCTGAATTGAG
                *         *         *         *         *         *    3710
                                                                       *
CCAGGGGATCATCAGAACTCAGGAAATTAGGCAAAAGCACCAGTCAAAGCTGTTTTGATTAGAAGCTTGC
                *         *         *         *         *         *    3780
                                                                       *
TGACCTATCCAGAGTAGGTGCTGAGAGGCCATTGACTGGGAATATGATGAATAATATGATTCAGTAGGTC
                *         *         *         *         *         *    3850
                                                                       *
ATGCGAGTCACTTTTGTACCAGGTGTTCTTTGTCATTGAGGCAATATCAATGTAAATTGTTGGCTAGGGT
                *         *         *         *         *         *    3920
                                                                       *
CTAAGAATGAATGAATACAATCCTAAGTCTTTGAATTAACTTATCCTTTAAAAGGATGTAGTTAGCTTCC
                *         *         *         *         *         *    3990
                                                                       *
AGAAAATAATTTGGTCAACATAGAATCACTTGTAGAAGTTGTGAAAAACTTGTAACTTTTCTCATAGCAC
                *         *         *         *         *         *    4060
                                                                       *
AATGATGACTCTGTCATCCTGTTTGAAACTTGCTACACATAGAACTGAAGTTAAACTTATTTGTAATGAA
                *         *         *         *         *         *    4130
                                                                       *
TGTATGTACACAATAGTATTTGCCATTTGGAAATTTATTGAACGAAGACCTGCAGGTCCCTCATAAATTA
                *         *         *         *         *         *    4200
                                                                       *
AAGATAACAGTGTTTACTATTAATTTAAATAAACATGTATTTTTATAGTTTTAGTATAATTATTCAATTA
                *         *         *         *         *         *    4270
                                                                       *
TAGATCTAGAAATAAGTAGATAAACATATATTGATAGGTAACAAAAGTGGTTTTTTAACTATATATATCA
                *         *         *         *         *         *    4340
                                                                       *
CAATCTCTACGACAATGTATTTATTGGAATTAATTTCTTTGTTGGTTTGTGTTTTCTGTAGGAAATTCTT
                *         *         *         *         *         *    4410
                                                                       *
GTTAAAAAAACATTAAAGTGGCTGGGCACAGTGGTTCATGCCTCTCATGCCTATAATCCCAACAGTTTGG
                *         *         *         *         *         *    4480
                                                                       *
GAGGCCAAGGTGGGAGGTTTACTTGAGGCCAGGAGTTTGAGACCAGCCTGGGCAACATAGCCAGACCCCA
```

Figure 1 Cont.

```
                                                                    4550
     *         *         *         *         *         *         *
TCTCCACAAAAAATAGAAAGATTAGCCAGATGTAGTGGCACGTGCCTGTAGTCCACGTGCCTGTAGTCCA
                                                                    4620
     *         *         *         *         *         *         *
GCTGCTTGGGAGGCTGAGATGAGAGGATTGCTTGAGTCCAGGCGTTCAAGGTTACAATGAGCTGTGGTCA
                                                                    4690
     *         *         *         *         *         *         *
CACTACTGCACCCCAGCCTGGGCAACAGAATGAGACCCTTTTCTAAGAAAAATAAAAAGGTAAAAAAAA
                                                                    4760
     *         *         *         *         *         *         *
AAAAAAGTCCTTTTTTTTTAAACGAGAGGAGGGAGTCCTTTTGCCTCTTATTGGTATGTTATAGGCAAT
                                                                    4830
     *         *         *         *         *         *         *
TTAGTGCTTCATCAGGCAGTAGCATCAAAAGTCTAATATGTAGAGGTAAATACGTAATGCCATTGATGTA
                                                                    4900
     *         *         *         *         *         *         *
TGACATTAATTTAATTTGAAATGAAGAAAACTTATTACCGGGAGTTATATTAATATCACTGCTACATTTA
                                                                    4970
     *         *         *         *         *         *         *
CGTTTAAGGTATAATGTTTTCCTTGAACAATGAATTCATTGACTCGTTCATAAGCCAAAATCTATACACA
                                                                    5040
     *         *         *         *         *         *         *
GTTTTTAAATTAATCAACAGGTGAAATTTGATTGTTTGTTTTTTAAAACGCCAACAGCCTGCTAGTCTG
                                                                    5110
     *         *         *         *         *         *         *
TCAGTGGTTGTCCTAATCAGAGATAATCTGGCACATCTCAAACCATTGAGGATTGGTCACAGAAAGATGT
                                                                    5180
     *         *         *         *         *         *         *
CATCATCCAGCATTGCGTCCACACAGTCAACAGTAGAGTTTGATAAATATATTTAATGAGTGCCTACTAT
                                                                    5250
     *         *         *         *         *         *         *
ATGCATCTGGGTCATGAGATAGTGATCCTATTCTCAAGGAGCATAAATTTGAACATTGTACGAACTAGGT
                                                                    5320
     *         *         *         *         *         *         *
GATATTTGTTACTAGAGTTTTGTTTGAACGTTTATTCTCTCATAAACATTTATTTAATACCTGCAGTGA
                                                                    5390
     *         *         *         *         *         *         *
TGAAGTTACTCTGCCATGTATTGGGATGGATTCCAAAGTGAGTAAGAGATAGTTTCTGCTTTTCCATTGC
```

Figure 1 Cont.

```
                                                                        5460
     *         *         *         *         *         *         *
TTGTAAATAAACAAGGTAGATGGGTAGGCATTATAATGCAATGAAAGCAGATTATGATATGTAGCATCAG
                                                                        5530
     *         *         *         *         *         *         *
ACAACTGTAAACAGAATGTAACAGGAGTTCTGAAGAGGAGATCATGTCCAGCCGAGTTGACCAGGACAAG
                                                                        5600
     *         *         *         *         *         *         *
TGACTTTTAAGTTTGGCCTAGATTGAGATAGAAATAAATGGAATTTTTATGATAAGATTATGTGACTATA
                                                                        5670
     *         *         *         *         *         *         *
CTACATACCAGGTATATTGACTTGGAGAATAATATTAATGAGTGATTGCAAAGCATGTATCTTGAAGTTC
                                                                        5740
     *         *         *         *         *         *         *
TTGTCTACATTTGCCTTTTTCTTTCCTTACGTTATTTACTACAGAAATTTTAAAAATGCAATCTACTACC
                                                                        5810
     *         *         *         *         *         *         *
TTAACATAAATTAATACATCTTAGAAGTAATGATAAAATTAAATTTACTATAATCATTATTGGCTGATAC
                                                                        5880
     *         *         *         *         *         *         *
TTGAATTGCCCTTGGAACGAGTTAAAGGTATCATAAACTTTCTGGGCTGGGCACGGTGCTCACGCCTGTA
                                                                        5950
     *         *         *         *         *         *         *
ATCCCAGCACTTTGGGAGGCCGAGGCGGGCGGATCACGAGGTCAGGAGATCGAGACCACGGTGAAACCCG
                                                                        6020
     *         *         *         *         *         *         *
GTCTCTACTAAAAATACAAAAAATTAGCTGGGCGCAGTGGCGGGCGCCTGTAGTCCCAGCTACTCGGGAG
                                                                        6090
     *         *         *         *         *         *         *
GCTGAGGCAGGAGAATGGCGTGAACCCGGGAGGCGGAGCTTGCAGTGAGCCGAGATGGCGCCACAGCACT
                                                                        6160
     *         *         *         *         *         *         *
CCAGCCTGGGCGACAGAGCGAGACTCCGTCTCAAAAAAAAAAAAAAAAAAAAGATATCATAAACTTCCTT
                                                                        6230
     *         *         *         *         *         *         *
AGGAGATTAATAAGGTCACGGGAGCTGATTGTAATATTTAGTTTCCCTCTGAATAGATTAATTTAAAGTA
                                                                        6300
     *         *         *         *         *         *         *
GTCATGTAATGTTTTTTTGGTTGCTTACAAATGTCTTTTTATTCCAAGCAGGACTATAATATGGATTTAG
                                                                     M  D  L>
```

Figure 1 Cont.

```
                                                                    6370
         *         *         *         *         *         *         *
AGCTCGACGAGTATTATAACAAGACACTTGCCACAGAGAATAATACTGCTGCCACTCGGAATTCTGATTT
 E  L  D  E  Y  Y  N  K  T  L  A  T  E  N  N  T  A  A  T  R  N  S  D  F>
                                                                    6440
         *         *         *         *         *         *         *
CCCAGTCTGGGATGACTATAAAAGCAGTGTAGATGACTTACAGTATTTTCTGATTGGGCTCTATACATTT
  P  V  W  D  D  Y  K  S  S  V  D  D  L  Q  Y  F  L  I  G  L  Y  T  F>
                                                                    6510
         *         *         *         *         *         *         *
GTAAGTCTTCTTGGCTTTATGGGGAATCTACTTATTTTAATGGCTCTCATGAAAAAGCGTAATCAGAAGA
  V  S  L  L  G  F  M  G  N  L  L  I  L  M  A  L  M  K  K  R  N  Q  K>
                                                                    6580
         *         *         *         *         *         *         *
CTACGGTAAACTTCCTCATAGGCAATCTGGCCTTTTCTGATATCTTGGTTGTGCTGTTTTGCTCACCTTT
  T  T  V  N  F  L  I  G  N  L  A  F  S  D  I  L  V  V  L  F  C  S  P  F>
                                                                    6650
         *         *         *         *         *         *         *
CACACTGACGTCTGTCTTGCTGGATCAGTGGATGTTTGGCAAAGTCATGTGCCATATTATGCCTTTTCTT
  T  L  T  S  V  L  L  D  Q  W  M  F  G  K  V  M  C  H  I  M  P  F  L>
                                                                    6720
         *         *         *         *         *         *         *
CAATGTGTGTCAGTTTTGGTTTCAACTTTAATTTTAATATCAATTGCCATTGTCAGGTATCATATGATAA
  Q  C  V  S  V  L  V  S  T  L  I  L  I  S  I  A  I  V  R  Y  H  M  I>
                                                                    6790
         *         *         *         *         *         *         *
AACATCCCATATCTAATAATTTAACAGCAAACCATGGCTACTTTCTGATAGCTACTGTCTGGACACTAGG
  K  H  P  I  S  N  N  L  T  A  N  H  G  Y  F  L  I  A  T  V  W  T  L  G>
                                                                    6860
         *         *         *         *         *         *         *
TTTTGCCATCTGTTCTCCCCTTCCAGTGTTTCACAGTCTTGTGGAACTTCAAGAAACATTTGGTTCAGCA
  F  A  I  C  S  P  L  P  V  F  H  S  L  V  E  L  Q  E  T  F  G  S  A>
                                                                    6930
         *         *         *         *         *         *         *
TTGCTGAGCAGCAGGTATTTATGTGTTGAGTCATGGCCATCTGATTCATACAGAATTGCCTTTACTATCT
  L  L  S  S  R  Y  L  C  V  E  S  W  P  S  D  S  Y  R  I  A  F  T  I>
                                                                    7000
         *         *         *         *         *         *         *
CTTTATTGCTAGTTCAGTATATTCTGCCCTTAGTTTGTCTTACTGTAAGTCATACAAGTGTCTGCAGAAG
  S  L  L  L  V  Q  Y  I  L  P  L  V  C  L  T  V  S  H  T  S  V  C  R  S>
                                                                    7070
         *         *         *         *         *         *         *
TATAAGCTGTGGATTGTCCAACAAAGAAAACAGACTTGAAGAAAATGAGATGATCAACTTAACTCTTCAT
  I  S  C  G  L  S  N  K  E  N  R  L  E  E  N  E  M  I  N  L  T  L  H>
                                                                    7140
         *         *         *         *         *         *         *
CCATCCAAAAAGAGTGGGCCTCAGGTGAAACTCTCTGGCAGCCATAAATGGAGTTATTCATTCATCAAAA
  P  S  K  K  S  G  P  Q  V  K  L  S  G  S  H  K  W  S  Y  S  F  I  K>
```

Figure 1 Cont.

```
                *         *         *         *         *         *    7210
                                                                         *
AACACAGAAGAAGATATATAGCAAGAAGACAGCATGTGTGTTACCTGCTCCAGAAAGACCTTCTCAAGAGAA
 K  H  R  R  R  Y  S  K  K  T  A  C  V  L  P  A  P  E  R  P  S  Q  E  N>
                *         *         *         *         *         *    7280
                                                                         *
CCACTCCAGAATACTTCCAGAAAACTTTGGCTCTGTAAGAAGTCAGCTCTCTTCATCCAGTAAGTTCATA
  H  S  R  I  L  P  E  N  F  G  S  V  R  S  Q  L  S  S  S  K  F  I>
                *         *         *         *         *         *    7350
                                                                         *
CCAGGGGTCCCCACTTGCTTTGAGATAAAACCTGAAGAAAATTCAGATGTTCATGAATTGAGAGTAAAAC
  P  G  V  P  T  C  F  E  I  K  P  E  E  N  S  D  V  H  E  L  R  V  K>
                *         *         *         *         *         *    7420
                                                                         *
GTTCTGTTACAAGAATAAAAAAGAGATCTCGAAGTGTTTTCTACAGACTGACCATACTGATATTAGTATT
  R  S  V  T  R  I  K  K  R  S  R  S  V  F  Y  R  L  T  I  L  I  L  V  F>
                *         *         *         *         *         *    7490
                                                                         *
TGCTGTTAGTTGGATGCCACTACACCTTTTCCATGTGGTAACTGATTTTAATGACAATCTTATTTCAAAT
  A  V  S  W  M  P  L  H  L  F  H  V  V  T  D  F  N  D  N  L  I  S  N>
                *         *         *         *         *         *    7560
                                                                         *
AGGCATTTCAAGTTGGTGTATTGCATTTGTCATTTGTTGGGCATGATGTCCTGTTGTCTTAATCCAATTC
  R  H  F  K  L  V  Y  C  I  C  H  L  L  G  M  M  S  C  C  L  N  P  I>
                *         *         *         *         *         *    7630
                                                                         *
TATATGGGTTTCTTAATAATGGGATTAAAGCTGATTTAGTGTCCCTTATACACTGTCTTCATATGTAATA
  L  Y  G  F  L  N  N  G  I  K  A  D  L  V  S  L  I  H  C  L  H  M>
                *         *         *         *         *         *    7700
                                                                         *
ATTCTCACTGTTTACCAAGGAAAGAACAAATGCTGGGGTCATATAAAATATATTTATGATAACTATTTAC
                *         *         *         *         *         *    7770
                                                                         *
ATATAATAAATAGAAATTTTGTTAACATGGAATTTAATTTATGTGAAAGAGTTCTGGATTCAAATGTCAG
                *         *         *         *         *         *    7840
                                                                         *
TTCATAATATATGGAAGATAATTTTATGTGTTATAGTAGGATTAATTTATTTAGTTGTGCAGTCAGTGTC
                *         *         *         *         *         *    7910
                                                                         *
AATCCAATCTGTAATTTCACTTTAGAAGGTTGTATTACCTTCCACTTCCATGTTGTCTTATAAACAAATG
                *         *         *         *         *         *    7980
                                                                         *
AATTGTATTTTTTGTTGAAAGTAAAAGTTATATCTAACCAACTCAGTACTTTTGTCCAAAAATATAATAA
                *         *         *         *         *         *    8050
                                                                         *
GAAAAAATTTTTCTCGAGGAACTTTTAATTTCAAACTTGAAGAATATCTACCAGCTATCTATATCATTTC
```

Figure 1 Cont.

```
                *         *         *         *         *         *   8120
                                                                        *
TACTCCATAGGCTTCTTAATGTTTAGTTTGTGAAGTACAGAAAAAATTTAATATGCCTGGAAAATCACAA
                *         *         *         *         *         *   8190
                                                                        *
CTAAATGACAGATGTATGCCCAAATTATGATTATAATCTTCAACATTAACTACAGTTTTGGAAGTCCTGT
                *         *         *         *         *         *   8260
                                                                        *
AGGAAAATGCTATTGCCTATTGAGAATTGGTCAAATTGTCAATTTAACTCCACTGTCCTAGTAATACACA
                *         *         *         *         *         *   8330
                                                                        *
AGTAATTTACCAAATAAAGAATTTTAAATCCTTTCCAGACTCATTATACAACATTAAACACTACCAATAA
                *         *         *         *
AAGTTGTTTTCATATACATCAAAACTATTCTAAAATGTGAA
```

SEQUENCE RANGE : 1 to 2143

Figure 2

```
                                                                    70
        *         *         *         *         *         *         *
AGCTCGTCGACCTGACCTGCCACAAAGTTAGAAGAAAGGATTGATTCAAGAAAGACTATAATATGGATTT
                                                                  M  D  L>

140
        *         *         *         *         *         *         *
AGAGCTCGACGAGTATTATAACAAGACACTTGCCACAGAGAATAATACTGCTGCCACTCGGAATTCTGAT
 E  L  D  E  Y  Y  N  K  T  L  A  T  E  N  N  T  A  A  T  R  N  S  D>

210
        *         *         *         *         *         *         *
TTCCCAGTCTGGGATGACTATAAAAGCAGTGTAGATGACTTACAGTATTTTCTGATTGGGCTCTATACAT
 F  P  V  W  D  D  Y  K  S  S  V  D  D  L  Q  Y  F  L  I  G  L  Y  T>

280
        *         *         *         *         *         *         *
TTGTAAGTCTTCTTGGCTTTATGGGGAATCTACTTATTTTAATGGCTCTCATGAAAAAGCGTAATCAGAA
 F  V  S  L  L  G  F  M  G  N  L  L  I  L  M  A  L  M  K  K  R  N  Q  K>

350
        *         *         *         *         *         *         *
GACTACGGTAAACTTCCTCATAGGCAATCTGGCCTTTTCTGATATCTTGGTTGTGCTGTTTTGCTCACCT
  T  T  V  N  F  L  I  G  N  L  A  F  S  D  I  L  V  V  L  F  C  S  P>

420
        *         *         *         *         *         *         *
TTCACACTGACGTCTGTCTTGCTGGATCAGTGGATGTTTGGCAAAGTCATGTGCCATATTATGCCTTTTC
 F  T  L  T  S  V  L  L  D  Q  W  M  F  G  K  V  M  C  H  I  M  P  F>

490
        *         *         *         *         *         *         *
TTCAATGTGTGTCAGTTTTGGTTTCAACTTTAATTTTAATATCAATTGCCATTGTCAGGTATCATATGAT
 L  Q  C  V  S  V  L  V  S  T  L  I  L  I  S  I  A  I  V  R  Y  H  M  I>

560
        *         *         *         *         *         *         *
AAAACATCCCATATCTAATAATTTAACAGCAAACCATGGCTACTTTCTGATAGCTACTGTCTGGACACTA
  K  H  P  I  S  N  N  L  T  A  N  H  G  Y  F  L  I  A  T  V  W  T  L>

630
        *         *         *         *         *         *         *
GGTTTTGCCATCTGTTCTCCCCTTCCAGTGTTTCACAGTCTTGTGGAACTTCAAGAAACATTTGGTTCAG
  G  F  A  I  C  S  P  L  P  V  F  H  S  L  V  E  L  Q  E  T  F  G  S>

700
        *         *         *         *         *         *         *
CATTGCTGAGCAGCAGGTATTTATGTGTTGAGTCATGGCCATCTGATTCATACAGAATTGCCTTTACTAT
  A  L  L  S  S  R  Y  L  C  V  E  S  W  P  S  D  S  Y  R  I  A  F  T  I>
```

Figure 2 Cont.

```
                                                                          770
         *         *         *         *         *         *         *
CTCTTTATTGCTAGTTCAGTATATTCTGCCCTTAGTTTGTCTTACTGTAAGTCATACAAGTGTCTGCAGA
  S  L  L  L  V  Q  Y  I  L  P  L  V  C  L  T  V  S  H  T  S  V  C  R>

840
         *         *         *         *         *         *         *
AGTATAAGCTGTGGATTGTCCAACAAAGAAAACAGACTTGAAGAAAATGAGATGATCAACTTAACTCTTC
  S  I  S  C  G  L  S  N  K  E  N  R  L  E  E  N  E  M  I  N  L  T  L>

910
         *         *         *         *         *         *         *
ATCCATCCAAAAAGAGTGGGCCTCAGGTGAAACTCTCTGGCAGCCATAAATGGAGTTATTCATTCATCAA
  H  P  S  K  K  S  G  P  Q  V  K  L  S  G  S  H  K  W  S  Y  S  F  I  K>

980
         *         *         *         *         *         *         *
AAAACACAGAAGAAGATATAGCAAGAAGACAGCATGTGTGTTACCTGCTCCAGAAAGACCTTCTCAAGAG
  K  H  R  R  R  Y  S  K  K  T  A  C  V  L  P  A  P  E  R  P  S  Q  E>

1050
         *         *         *         *         *         *         *
AACCACTCCAGAATACTTCCAGAAAACTTTGGCTCTGTAAGAAGTCAGCTCTCTTCATCCAGTAAGTTCA
  N  H  S  R  I  L  P  E  N  F  G  S  V  R  S  Q  L  S  S  S  K  F>

1120
         *         *         *         *         *         *         *
TACCAGGGGTCCCCACTTGCTTTGAGATAAAACCTGAAGAAAATTCAGATGTTCATGAATTGAGAGTAAA
  I  P  G  V  P  T  C  F  E  I  K  P  E  E  N  S  D  V  H  E  L  R  V  K>

1190
         *         *         *         *         *         *         *
ACGTTCTGTTACAAGAATAAAAAAGAGATCTCGAAGTGTTTTCTACAGACTGACCATACTGATATTAGTA
  R  S  V  T  R  I  K  K  R  S  R  S  V  F  Y  R  L  T  I  L  I  L  V>

1260
         *         *         *         *         *         *         *
TTTGCTGTTAGTTGGATGCCACTACACCTTTTCCATGTGGTAACTGATTTTAATGACAATCTTATTTCAA
  F  A  V  S  W  M  P  L  H  L  F  H  V  V  T  D  F  N  D  N  L  I  S>

1330
         *         *         *         *         *         *         *
ATAGGCATTTCAAGTTGGTGTATTGCATTTGTCATTTGTTGGGCATGATGTCCTGTTGTCTTAATCCAAT
  N  R  H  F  K  L  V  Y  C  I  C  H  L  L  G  M  M  S  C  C  L  N  P  I>

1400
         *         *         *         *         *         *         *
TCTATATGGGTTTCTTAATAATGGGATTAAAGCTGATTTAGTGTCCCTTATACACTGTCTTCATATGTAA
  L  Y  G  F  L  N  N  G  I  K  A  D  L  V  S  L  I  H  C  L  H  M>
```

Figure 2 Cont.

```
                                                                    1470
         *         *         *         *         *         *         *
TAATTCTCACTGTTTACCAAGGAAAGAACAAATGCTGGGGTCATATAAAATATATTTATGATAACTATTT

1540
         *         *         *         *         *         *         *
ACATATAATAAATAGAAATTTTGTTAACATGGAATTTAATTTATGTGAAAGAGTTCTGGATTCAAATGTC

1610
         *         *         *         *         *         *         *
AGTTCATAATATATGGAAGATAATTTTATGTGTTATAGTAGGATTAATTTATTTAGTTGTGCAGTCAGTG

1680
         *         *         *         *         *         *         *
TCAATCCAATCTGTAATTTCACTTTAGAAGGTTGTATTACCTTCCACTTCCATGTTGTCTTATAAACAAA

1750
         *         *         *         *         *         *         *
TGAATTGTATTTTTTGTTGAAAGTAAAAGTTATATCTAACCAACTCAGTACTTTTGTCCAAAAATATAAT

1820
         *         *         *         *         *         *         *
AAGAAAAAATTTTTCTCGAGGAACTTTTAATTTCAAACTTGAAGAATATCTACCAGCTATCTATATCATT

1890
         *         *         *         *         *         *         *
TCTACTCCATAGGCTTCTTAATGTTTAGTTTGTGAAGTACAGAAAAAATTTAATATGCCTGGAAAATCAC

1960
         *         *         *         *         *         *         *
AACTAAATGACAGATGTATGCCCAAATTATGATTATAATCTTCAACATTAACTACAGTTTTGGAAGTCCT

2030
         *         *         *         *         *         *         *
GTAGGAAAATGCTATTGCCTATTGAGAATTGGTCAAATTGTCAATTTAACTCCACTGTCCTAGTAATACA

2100
         *         *         *         *         *         *         *
CAAGTAATTTACCAAATAAAGAATTTTAAATCCTTTCCAGACTCATTATACAACATTAAACACTACCAAT

*         *         *         *
AAAAGTTGTTTTCATATACATCAAAACTATTCTAAAATGTGAA
```

Figure 3

SEQUENCE RANGE : 1 to 2286

```
                *         *         *         *         *         *         70
                                                                              *
GAATTCGGCACGAGGGGTTTGCAAGGTGGCTTGGAAGTCAACTGCCAGTAGGAAATAGCCATCCACACAC

*         *         *         *         *         *         140
                                                                              *
CTGAGTTCCAAGGGGGAAGAAAGAGATTCTTATCTGATTCTAGTATGGAGTTTAAGCTTGAGGAGCATTT
                                                  M  E  F  K  L  E  E  H  F>

*         *         *         *         *         *         210
                                                                              *
TAACAAGACATTTGTCACAGAGAACAATACAGCTGCTGCTCGGAATGCAGCCTTCCCTGCCTGGGAGGAC
 N  K  T  F  V  T  E  N  N  T  A  A  A  R  N  A  A  F  P  A  W  E  D>

*         *         *         *         *         *         280
                                                                              *
TACAGAGGCAGCGTAGACGATTTACAATACTTTCTGATTGGGCTCTATACATTCGTAAGTCTTCTTGGCT
 Y  R  G  S  V  D  D  L  Q  Y  F  L  I  G  L  Y  T  F  V  S  L  L  G>

*         *         *         *         *         *         350
                                                                              *
TTATGGGCAATCTACTTATTTTAATGGCTGTTATGAAAAAGCGCAATCAGAAGACTACAGTGAACTTTCT
 F  M  G  N  L  L  I  L  M  A  V  M  K  K  R  N  Q  K  T  T  V  N  F  L>

*         *         *         *         *         *         420
                                                                              *
CATAGGCAACCTGGCCTTCTCCGACATCTTGGTCGTCCTGTTTTGCTCCCCTTTCACCCTGACCTCTGTC
  I  G  N  L  A  F  S  D  I  L  V  V  L  F  C  S  P  F  T  L  T  S  V>

*         *         *         *         *         *         490
                                                                              *
TTGTTGGATCAGTGGATGTTTGGCAAAAGCATGTGCCATATCATGCCGTTCCTTCAATGTGTGTCAGTTC
  L  L  D  Q  W  M  F  G  K  S  M  C  H  I  M  P  F  L  Q  C  V  S  V>

*         *         *         *         *         *         560
                                                                              *
TGGTTTCAACTCTGATTTTAATATCAATTGCCATTGTCAGGTATCATATGATAAAGCACCCTATTTCTAA
  L  V  S  T  L  I  L  I  S  I  A  I  V  R  Y  H  M  I  K  H  P  I  S  N>

*         *         *         *         *         *         630
                                                                              *
CAATTTAACGGCAAACCATGGCTACTTCCTGATAGCTACTGTCTGGACACTGGGCTTTGCCATCTGTTCT
  N  L  T  A  N  H  G  Y  F  L  I  A  T  V  W  T  L  G  F  A  I  C  S>

*         *         *         *         *         *         700
                                                                              *
CCCCTCCCAGTGTTTCACAGTCTTGTGGAACTTAAGGAGACCTTTGGCTCAGCACTGCTGAGTAGCAAAT
  P  L  P  V  F  H  S  L  V  E  L  K  E  T  F  G  S  A  L  L  S  S  K>
```

Figure 3 Cont.

```
                                                                    770
       *         *         *         *         *         *         *
ATCTCTGTGTTGAGTCATGGCCCTCTGATTCATACAGAATTGCTTTCACAATCTCTTTATTGCTAGTGCA
 Y  L  C  V  E  S  W  P  S  D  S  Y  R  I  A  F  T  I  S  L  L  L  V  Q>

840
       *         *         *         *         *         *         *
GTATATCCTGCCTCTAGTATGTTTAACGGTAAGTCATACCAGCGTCTGCCGAAGCATAAGCTGTGGATTG
  Y  I  L  P  L  V  C  L  T  V  S  H  T  S  V  C  R  S  I  S  C  G  L>

910
       *         *         *         *         *         *         *
TCCCACAAAGAAAACAGACTCGAAGAAAATGAGATGATCAACTTAACCCTACAGCCATCCAAAAAGAGCA
  S  H  K  E  N  R  L  E  E  N  E  M  I  N  L  T  L  Q  P  S  K  K  S>

980
       *         *         *         *         *         *         *
GGAACCAGGCAAAAACCCCCAGCACTCAAAAGTGGAGCTACTCATTCATCAGAAAGCACAGAAGGAGGTA
  R  N  Q  A  K  T  P  S  T  Q  K  W  S  Y  S  F  I  R  K  H  R  R  Y>

1050
       *         *         *         *         *         *         *
CAGCAAGAAGACGGCCTGTGTCTTACCCGCCCCAGCAGGACCTTCCCAGGGGAAGCACCTAGCCGTTCCA
  S  K  K  T  A  C  V  L  P  A  P  A  G  P  S  Q  G  K  H  L  A  V  P>

1120
       *         *         *         *         *         *         *
GAAAATCCAGCCTCCGTCCGTAGCCAGCTGTCGCCATCCAGTAAGGTCATTCCAGGGGTCCCAATCTGCT
  E  N  P  A  S  V  R  S  Q  L  S  P  S  S  K  V  I  P  G  V  P  I  C>

1190
       *         *         *         *         *         *         *
TTGAGGTGAAACCTGAAGAAAGCTCAGATGCTCATGAGATGAGAGTCAAGCGTTCCATCACTAGAATAAA
  F  E  V  K  P  E  E  S  S  D  A  H  E  M  R  V  K  R  S  I  T  R  I  K>

1260
       *         *         *         *         *         *         *
AAAGAGATCTCGAAGTGTTTTCTACAGACTGACCATACTGATACTCGTGTTCGCCGTTAGCTGGATGCCA
  K  R  S  R  S  V  F  Y  R  L  T  I  L  I  L  V  F  A  V  S  W  M  P>

1330
       *         *         *         *         *         *         *
CTCCACGTCTTCCACGTGGTGACTGACTTCAATGATAACTTGATTTCCAATAGGCATTTCAAGCTGGTAT
  L  H  V  F  H  V  V  T  D  F  N  D  N  L  I  S  N  R  H  F  K  L  V>

1400
       *         *         *         *         *         *         *
ACTGCATCTGTCACTTGTTAGGCATGATGTCCTGTTGTCTAAATCCGATCCTATATGGTTTCCTTAATAA
  Y  C  I  C  H  L  L  G  M  M  S  C  C  L  N  P  I  L  Y  G  F  L  N  N>

1470
       *         *         *         *         *         *         *
TGGTATCAAAGCAGACTTGAGAGCCCTTATCCACTGCCTACACATGTCATGATTCTCTCTGTGCACCAAA
   G  I  K  A  D  L  R  A  L  I  H  C  L  H  M  S>
```

Figure 3 Cont.

```
                *         *         *         *         *         *    1540
                                                                        *
GAGAGAAGAAACGTGGTAATTGACACATAATTTATACAGAAGTATTCTGGATCTGAATGCCAGTTCGTAA

*         *         *         *         *         *    1610
                                                                        *
TCTACGTAAGATCATCTTCATGTTATAATATGGTTAATTCAATCAGTTGTGCAGAGTCAATGTCCATCTA

*         *         *         *         *         *    1680
                                                                        *
ATACAATTTCATGTGTTGAAGTAGTTTACATTATTTTCCATTTTATGTCATTGGTAATAAGTTGAGTGAT

*         *         *         *         *         *    1750
                                                                        *
ACTCTGTGGTTTAGTGTAAAATGTATGAAGTGACAAGTTGTCCCAAAGAGCATTTAACTACAGATTTAAG

*         *         *         *         *         *    1820
                                                                        *
GAATTTCTATTATCTGGGTATCTTCATTTCTATTTCACAGGCTTCTTAACATTTTTTTGTAAAAGTACAA

*         *         *         *         *         *    1890
                                                                        *
AAATATTCAAAAGTCAGAACTCTATTACAGATGTATGCATAAAAGATGATTATAATTTTGTAGGAGAAAG

*         *         *         *         *         *    1960
                                                                        *
ATCTGCTCCTATTAGTGAAGATTGGTAAAATTGTCAGTTTAACCCGTCTGTCCTACTACTAATATTTAAT

*         *         *         *         *         *    2030
                                                                        *
TTTTCAAATATGAAAAGGTTTCAGATTTTGTTTAGATTTATATCACATTAAACACTGTCAAATAAAGGCT

*         *         *         *         *         *    2100
                                                                        *
GTTTTTATATGCATCGTTGATGTTCCAAAATGTGAAGTCTAAATGGTGTCTGTATTTCCAATTATTAAAT

*         *         *         *         *         *    2170
                                                                        *
AACTTCTAAGATCATTTTTAAAAGTCTGTAGATGGTATGGATAGCTAGTTGTTTGTTAATATAAAGTAAA

*         *         *         *         *         *    2240
                                                                        *
AGTAGATAGCTGATTTATGTTGTACCTATGTCGTATGTATATTAGGAGCAGTTTCAGCCCCACAGAACAC

*         *         *         *
TCTATCGTGTTGTCTCACTAAAGTGAAAGCAAACGAAAAAAAAAA
```

Figure 4

SEQUENCE RANGE: 1 to 1585

```
                                                                          70
GTTATTGTCATAGCGTGCTATTGTTCTTCAAGCTGCTAATGGTCACTGTCTTCTTCCAAGCAGGACTCTA

140
GTATGGAGGTTAAACTTGAAGAGCATTTTAACAAGACATTTGTCACGGAGAACAATACTGCTGCCAGTCA
  M  E  V  K  L  E  E  H  F  N  K  T  F  V  T  E  N  N  T  A  A  S  Q>

210
GAACACGGCCTCCCCTGCCTGGGAGGACTACAGAGGCACAGAGAACAATACTTCTGCTGCTCGGAACACT
  N  T  A  S  P  A  W  E  D  Y  R  G  T  E  N  N  T  S  A  A  R  N  T>

280
CCGTTTCCAGTCTGGGAGGACTATAGAGGCAGCGTAGACGACTTACAATACTTCCTGATTGGGCTCTATA
  P  F  P  V  W  E  D  Y  R  G  S  V  D  D  L  Q  Y  F  L  I  G  L  Y>

350
CATTTGTAAGTCTTCTTGGTTTTATGGGAAATCTACTTATCTTAATGGCTGTTATGAAAAAGCGCAATCA
  T  F  V  S  L  L  G  F  M  G  N  L  L  I  L  M  A  V  M  K  K  R  N  Q>

420
GAAGACTACAGTGAACTTTCTCATAGGCAACCTGGCCTTCTCCGACATTTTGGTTGTCCTGTTTTGCTCC
  K  T  T  V  N  F  L  I  G  N  L  A  F  S  D  I  L  V  V  L  F  C  S>

490
CCTTTCACCCTGACCTCTGTCTTGTTGGATCAGTGGATGTTCGGCAAAGCCATGTGCCATATCATGCCAT
  P  F  T  L  T  S  V  L  L  D  Q  W  M  F  G  K  A  M  C  H  I  M  P>

560
TCCTTCAGTGTGTATCAGTTCTGGTTTCAACTCTGATTTTAATATCGATTGCCATTGTCAGGTATCATAT
  F  L  Q  C  V  S  V  L  V  S  T  L  I  L  I  S  I  A  I  V  R  Y  H  M>

630
GATAAAGCACCCTATATCTAACAATTTAACAGCAAACCATGGCTACTTCCTGATAGCATCTGTCTGGACA
  I  K  H  P  I  S  N  N  L  T  A  N  H  G  Y  F  L  I  A  S  V  W  T>

700
CTGGGCTTTGCCATCTGTTCTCCCCTCCCAGTGTTTCACAGCCTTGTGGAACTTAAGGAAACCTTTGGCT
  L  G  F  A  I  C  S  P  L  P  V  F  H  S  L  V  E  L  K  E  T  F  G>

770
CAGCATTGCTAAGCAGCAAGTATTTGTGTGTTGAGTCATGGCCCTCTGATTCATACAGAATTGCTTTCAC
  S  A  L  L  S  S  K  Y  L  C  V  E  S  W  P  S  D  S  Y  R  I  A  F  T>

840
AATCTCTTTATTGTTAGTTCAGTATATCCTGCCTCTAGTATGTTTAACAGTAAGTCATACTAGTGTCTGC
  I  S  L  L  L  V  Q  Y  I  L  P  L  V  C  L  T  V  S  H  T  S  V  C>
```

Figure 4 cont.

```
                                                                     910
       *         *         *         *         *         *         *
AGGAGTATAAGCTGTGGATTGTCCCACAAAGAAAACAGACTCGAAGAAAATGAGATGATCAACTTAACTC
 R  S  I  S  C  G  L  S  H  K  E  N  R  L  E  E  N  E  M  I  N  L  T>

980
       *         *         *         *         *         *         *
TACATCCATCCAAAAAGAGTCGGGACCAGGCAAAACTCCCCAGCACTCAAAAGTGGAGCTACTCATTCAT
 L  H  P  S  K  K  S  R  D  Q  A  K  L  P  S  T  Q  K  W  S  Y  S  F  I>

1050
       *         *         *         *         *         *         *
CAGAAAGCACCGAAGAAGGTACAGCAAGAAGACGGCATGCGTGTTACCCGCCCCAGCAGGACCTTCCCAG
  R  K  H  R  R  R  Y  S  K  K  T  A  C  V  L  P  A  P  A  G  P  S  Q>

1120
       *         *         *         *         *         *         *
GAGAAGCACCTAACCGTTCCAGAAAACCCAGGCTCGGTCCGTAGCCAGCTGTCACCATCCAGTAAGGTTA
 E  K  H  L  T  V  P  E  N  P  G  S  V  R  S  Q  L  S  P  S  S  K  V>

1190
       *         *         *         *         *         *         *
TTCCAGGGGTCCCGATCTGCTTTGAGGTGAAACCTGAAGAAAGCTCAGATGCTCAGGAGATGAGAGTCAA
 I  P  G  V  P  I  C  F  E  V  K  P  E  E  S  S  D  A  Q  E  M  R  V  K>

1260
       *         *         *         *         *         *         *
GCGTTCCCTCACGAGAATAAAGAAGAGATCTCGCAGTGTTTTCTACAGACTGACTATATTGATATTAGTG
 R  S  L  T  R  I  K  K  R  S  R  S  V  F  Y  R  L  T  I  L  I  L  V>

1330
       *         *         *         *         *         *         *
TTCGCTGTTAGCTGGATGCCACTCCACGTCTTCCACGTGGTGACCGATTTCAATGATAACCTGATTTCCA
 F  A  V  S  W  M  P  L  H  V  F  H  V  V  T  D  F  N  D  N  L  I  S>

1400
       *         *         *         *         *         *         *
ATAGGCATTTCAAGCTGGTGTACTGCATCTGTCACTTGTTAGGCATGATGTCCTGTTGTCTTAATCCGAT
 N  R  H  F  K  L  V  Y  C  I  C  H  L  L  G  M  M  S  C  C  L  N  P  I>

1470
       *         *         *         *         *         *         *
CTTATATGGATTCCTTAATAATGGTATCAAAGCAGACTTGAGAGCCCTTATCCACTGCCTACACATGTCA
  L  Y  G  F  L  N  N  G  I  K  A  D  L  R  A  L  I  H  C  L  H  M  S>

1540
       *         *         *         *         *         *         *
TGATTCTCTCTGTGCACCGAGGAGAGAAGAAATGTGGAGACTGCCCACAATACATCTGTGCTAATTGATG

*         *         *         *
CATAATTTACATAAACGTGTCTGGATCTGAATGCCAGTTTGTAAT
```

| | | | |
|---|---|---|---|
| human Y5 | 1 | MDLELDEYYNKTLA------------------- | 14 |
| rat Y5 | 1 | MEFKLEEHFNKTFV------------------- | 14 |
| mouse Y5 | 1 | MEVKLEEHFNKTFVTENNTAASQNTASPAWEDYR | 34 |
| human Y5 | 15 | -TENNTAAIRNSDFPVWDDYKSSVDDLQYFLIGL | 47 |
| rat Y5 | 15 | -TENNTAAARNAAFPAWEDYRGSVDDLQYFLIGL | 47 |
| mouse Y5 | 35 | GTENNTSAARNTPFPVEDDYRGSVDDLQYFLIGL | 68 |
| human Y5 | 48 | YTFVSLLGFMGNLLILMALMKKRNQKTTVNFLIG | 81 |
| rat Y5 | 48 | YTFVSLLGFMGNLLILMAVMKKRNQKTTVNFLIG | 81 |
| mouse Y5 | 69 | YTFVSLLGFMGNLLILMAVMKKRNQKTTVNFLIG | 102 |
| human Y5 | 82 | NLAFSDILVVLFCSPFTLTSVLLDQWMFGKVMCH | 115 |
| rat Y5 | 82 | NLAFSDILVVLFCSPFTLTSVLLDQWMFGKSMCH | 115 |
| mouse Y5 | 103 | NLAFSDILVVLFCSPFTLTSVLLDQWMFGKAMCH | 136 |
| human Y5 | 116 | IMPFLQCVSVLVSTLILISIAIVRYHMIKHPISN | 149 |
| rat Y5 | 116 | IMPFLQCVSVLVSTLILISIAIVRYHMIKHPISN | 149 |
| mouse Y5 | 137 | IMPFLQCVSVLVSTLILISIAIVRYHMIKHPISN | 170 |
| human Y5 | 150 | NLTANHGYFLIATVWTLGFAICSPLPVFHSLVEL | 183 |
| rat Y5 | 150 | NLTANHGYFLIATVWTLGFAICSPLPVFHSLVEL | 183 |
| mouse Y5 | 171 | NLTANHGYFLIASVWTLGFAICSPLPVFHSLVEL | 204 |
| human Y5 | 184 | QETFGSALLSSRYLCVESWPSDSYRIAFTISLLL | 217 |
| rat Y5 | 184 | KETFGSALLSSKYLCVESWPSDSYRIAFTISLLL | 217 |
| mouse Y5 | 205 | KETFGSALLSSKYLCVESWPSDSYRIAFTISLLL | 238 |
| human Y5 | 218 | VQYILPLVCLTVSHTSVCRSISCGLSNKENRLEE | 251 |
| rat Y5 | 218 | VQYILPLVCLTVSHTSVCRSISCGLSHKENRLEE | 251 |
| mouse Y5 | 239 | VQYILPLVCLTVSHTSVCRSISCGLSHKENRLEE | 272 |
| human Y5 | 252 | NEMINLTLHPSKKSGPQVKLSGSHKWSYSFIKKH | 285 |
| rat Y5 | 252 | NEMINLTLHPSKKSRNQAKTPSTQKWSYSFIRKH | 285 |
| mouse Y5 | 273 | NEMINLTLHPSKKSRDQAKLPSTQKWSYSFRKKH | 306 |
| human Y5 | 286 | RRRYSKKTACVLPAPERPSQENHSRILPENFGSV | 319 |
| rat Y5 | 286 | RRRYSKKTACVLPAPAGPSQEKHL-AVPENPASV | 318 |
| mouse Y5 | 307 | RRRYSKKTACVLPAPAGPSQEKHL-TVPENPGSV | 339 |
| human Y5 | 320 | RSQLSSSSKEIPGVPTCFELKPEENSDVHELRVK | 353 |
| rat Y5 | 319 | RSQLSPSSKVIPGVPICFEVKPEESSDAHEMRVK | 352 |
| mouse Y5 | 340 | RSQLSPSSKVIPGVPICFEVKPEESSDAQEMRVK | 373 |
| human Y5 | 354 | RSVTRIKKRSRSVFYRLTILILVFAVSWMPLHLF | 387 |
| rat Y5 | 353 | RSITRIKKRSRSVFYRLTILILVFAVSWMPLHVF | 386 |
| mouse Y5 | 374 | RSLTRIKKRSRSVFYRLTILILVFAVSWMPLHVF | 407 |
| human Y5 | 388 | HVVTDFNDNLISNRHFKLVYCICHLLGMMSCCLN | 421 |
| rat Y5 | 387 | HVVTDFNDNLISNRHFKLVYCICHLLGMMSCCLN | 420 |
| mouse Y5 | 408 | HVVTDFNDNLISNRHFKLVYCICHLLGMMSCCLN | 441 |
| human Y5 | 422 | PILYGFLNNGIKADLVSLIHCLHM | 445 |
| rat Y5 | 421 | PILYGFLNNGIKADLRALIHCLHMS | 445 |
| mouse Y5 | 442 | PILYGFLNNGIKADLRALIHCLHMS | 466 |

Figure 5

SEQUENCE LISTING

<160> NUMBER OF SEQ ID NOS: 8

<210> SEQ ID NO 1
<211> LENGTH: 8371
<212> TYPE: DNA
<213> ORGANISM: Homo sapiens

<400> SEQUENCE: 1

| | | | | | |
|---|---|---|---|---|---:|
| ctgcagcggc | cggggcgccc | cgaggtacgg | gctcccgccc | ctccctgcca | accccttcg | 60 |
| cgccgggtag | gcctgcaccg | aggggccgtg | gcgggtcccc | gcgcgggctg | cgagtctgcg | 120 |
| caggtccctg | ggagcccgca | cccgtctctg | gtgccagggc | gttgtcgggg | gtcccaagag | 180 |
| agcggggtgg | ggaaggtgaa | gggagcgcgg | ctggaaaaat | ggggattagg | gtggcggaac | 240 |
| aggcacttgt | caggagtgaa | gagacagcgg | agagggtact | gggctgaatt | ctttcgtgcc | 300 |
| gagcaggtcc | ctccggttcc | caactcaccc | gggtggagca | ggcgcgggcc | gaacccggga | 360 |
| ggagagtgtc | gggatccgc | gaaggagcct | cctgggatg | gggcggggga | tggacaaagc | 420 |
| gctgccccg | gctggacacg | ctctggcgct | agcccggctg | gcatccggag | ctgggaacag | 480 |
| caccccgcgg | ggtgcccggg | tcagggctca | acctagcggg | tctctggcga | ggccgggggc | 540 |
| gcagcccgcg | gggcgccact | caggccgtcc | agctgccgcg | cggtccagcg | ctgacccgag | 600 |
| cccgggaggc | agctgcgctc | taaggtttgc | gctcctgttt | gcgaggtgtc | ttcatataac | 660 |
| aaatgcgagc | aataacaaac | atccatagaa | ctcgaattcc | agaaacggga | attctttttt | 720 |
| ccaagttcac | agacctttag | ttaatctttt | aaaggaactg | aggcgttgtg | ttggaccaaa | 780 |
| gccaaaacga | ttttaccta | caccatgaaa | atagcctaa | ggctcttttc | agcagaattt | 840 |
| ttggcagtcc | gaatgcaatt | tttagatttc | agatttctca | agggaagaga | aactctgctg | 900 |
| ttagaatttg | gaagggaggg | tggtgcatgc | ctgtgtgttt | gtcagctgag | cagagctgta | 960 |
| tttatctttc | caattcaaat | tgtgccagat | tctggcttta | agaaaaaacc | atgggaatat | 1020 |
| ttgagaacat | ggaatcatgc | tgctgttcca | cgatcacagc | aaaacagaca | atagttgata | 1080 |
| ttgtatcatt | gcaggaggaa | aaagaattac | atatatttta | ttcttttgtg | tgattgtcat | 1140 |
| cctttgtgaa | aagaatgatg | tgtatttca | taaagcaaaa | aattattcaa | acaaagaaac | 1200 |
| cttatttaaa | tgtacaagtc | agacttttaa | tatcctttga | attccctgca | gttcctccta | 1260 |
| ttattcttga | gaactatcta | cttggttaaa | atacttaaat | ctattcagaa | ggtttcattt | 1320 |
| gtctaggtct | cagatataga | agagtttata | agaaaattcc | agtaaacctt | taaaaagata | 1380 |
| ttatttttta | taagttgcca | tagtttaata | aagaactttt | attttcaca | cttttactc | 1440 |
| agagattaaa | gttctgtgtt | tcagcctgga | aattctgatg | gtgggagata | caactaatac | 1500 |
| aaaagagaat | gagtaaatat | agtaattagg | tatgacaaaa | gtctcatgct | gtcaatatca | 1560 |
| gatttcttgt | caaataatat | tccatgttaa | aatatttttt | ctctggctat | atttcataat | 1620 |
| ttatatagca | atttcagaag | attcacatat | atcattactt | ttataataga | taaaatatgt | 1680 |
| tgcataaaaa | tgacagcact | cgtaataaca | cttgttgaaa | tttggatttc | cattgtaggt | 1740 |
| ctgctcattg | tgttttcagg | aaaaaggaag | ggaaagggta | agtttaatgg | aaaaaatcct | 1800 |
| gcttttttgt | ttgtttttc | atttaagtgc | gttcctgtac | cttgagtttt | caagttaaat | 1860 |
| cttattgtac | aaaattttcc | taatgtttaa | actaggccct | ggctaccagg | aggcactttt | 1920 |
| aaaaaaacta | cacgtccacc | accacccctc | ccccaccgc | cctccctgcc | tcagcattt | 1980 |
| gcaatattca | ttatttagtt | gtaagaagaa | attcttcctt | cattggagca | agattcaca | 2040 |

-continued

```
gaatgttcat tctgtgcaga ctatatatta gatattacat gtgtgtatgt ttatgtggta    2100
gatggtgtgg ggtggggcta gagggagagc aggagaaagt tgactacagt cacaccaaaa    2160
taaaatgaat aaatgagtgt tgaatgaatc aagtgctaag agagaatttt taaattgctt    2220
accaatctat cagtagctac ataagtattc attatattca gcagtaatgc atgtgtccat    2280
gctatagaga aataatatat tactatcagt caggagaatg ccattcattt attaattcat    2340
tcatcatcca atttgggcct ttttatatct cagcaatcta cagttactca gggtgtagag    2400
cttgaattaa tctatataga atattcttgg catagcacct tgcattagtc gtctttatgc    2460
ttagagcaga gcagagcacc tagcagaata tatgttcaat aaatacttttt tgaatgaata    2520 aaagaaggaa caactaatca ttcttagctg ttcattaata gaaggtgcct acccctttaa    2580
aattatatat aaattatctc tttcttaaaa tactcaaatg ttttaaggaa tgaaagaagc    2640
atcctcagtt ttttctccag tgtccaatga atactcaaga tggcatttat ttcatcttct    2700
tactaaggag atgtggtttt acaatttaat gcattcaata ttttatgtgc atatatttaa    2760
aataaaagtt ttaataacag actgcacagt cgcggaaatg gatatacttc tttttttcatt    2820 tacatttttt aaatgttgta aatatatctt acagttttag ttgcatgttg cttgtgtgat    2880
agcctttatc aatgaagtta tccaaattta aagtgctaaa ctatctttat tgtctgtcta    2940
ggtatctcct cctcattgca ttttgggggcc atttgaaaca tctataattt caatggttct    3000
ctataaatgt atatataaag atacatatac acacatatat atgtacacac aaaaatatag    3060
tcatactcta tcctgaattt tcccacattg ccagaatgat tcatttctgt tattttaaag    3120
caagggaaat taaactgctt ttctaaaacg attggtaaga aatatttact tagcatccac    3180
tatgtgtaat atgctttatt aaacatcatt tctagaatga aaataattaa gagttttatc    3240
tccattcgaa tataatagag aggtctaacc acatggaatg gagaaaaatc tgaattttag    3300
actcaaaact acattgtttc tattaccaca aattgtgctg catcttctct ttcttcaaaa    3360
aattttggac agcaatttta cactaagtaa gtatcatcca cagttacatg ttccaaaaag    3420
gcacaaagcc gttgtagaag gggccatcta atttctctct tgttcttgct taggtgttac    3480
aaggaaaggc tatcggtaac aactgacctg ccacaaagtt agaagaaagg attgattcaa    3540
gaaagtaagt caagagaaga acaactaagc aggattgcag ttacaagcag cctgtacaca    3600
attataaata taaataggat catgaataag ctgaattgag ccaggggatc atcagaactc    3660
aggaaattag gcaaaagcac cagtcaaagc tgttttgatt agaagcttgc tgacctatcc    3720
agagtaggtg ctgagaggcc attgactggg aaatatgatga ataatatgat tcagtaggtc    3780
atgcgagtca cttttgtacc aggtgttctt tgtcattgag gcaatatcaa tgtaaattgt    3840
tggctagggt ctaagaatga atgaatacaa tcctaagtct ttgaattaac ttatcccttta    3900 aaaggatgta gttagcttcc agaaaataat ttggtcaaca tagaatcact tgtagaagtt    3960
gtgaaaaact tgtaactttt ctcatagcac aatgatgact ctgtcatcct gtttgaaact    4020
tgctacacat agaactgaag ttaaacttat ttgtaatgaa tgtatgtaca caatagtatt    4080
tgccatttgg aaatttattg aacgaagacc tgcaggtccc tcataaatta aagataacag    4140
tgtttactat taatttaaat aaacatgtat ttttatagtt ttagtataat tattcaatta    4200
tagatctaga aataagtaga taaacatata ttgataggta acaaaagtgg ttttttaact    4260
atatatatca caatctctac gacaatgtat ttattggaat taatttctttt gttggtttgt    4320 gtttttctgta ggaaattctt gttaaaaaaa cattaaagtg gctgggcaca gtggttcatg    4380
```

-continued

```
cctctcatgc ctataatccc aacagtttgg gaggccaagg tgggaggttt acttgaggcc    4440
aggagtttga gaccagcctg gcaacatag ccagacccca tctccacaaa aaatagaaag    4500
attagccaga tgtagtggca cgtgcctgta gtccacgtgc ctgtagtcca gctgcttggg    4560
aggctgagat gagaggattg cttgagtcca ggcgttcaag gttacaatga gctgtggtca    4620
cactactgca ccccagcctg gcaacagaa tgagacccct tttctaagaa aaataaaaag    4680
gtaaaaaaaa aaaaaagtcc tttttttttt aaacgagagg agggagtcct tttgcctctt    4740
attggtatgt tataggcaat ttagtgcttc atcaggcagt aggatcaaaa gtctaatatg    4800
tagaggtaaa tacgtaatgc cattgatgta tgacattaat ttaatttgaa atgaagaaaa    4860
cttattaccg ggagttatat taatatcact gctacattta cgtttaaggt ataatgtttt    4920
ccttgaacaa tgaattcatt gactcgttca taagccaaaa tctatacaca gtttttaaat    4980
taatcaacag gtgaaatttg attgtttgtt tttttaaaac gccaacagcc tgctagtctg    5040
tcagtggttg tcctaatcag agataatctg gcacatctca aaccattgag gattggtcac    5100
agaaagatgt catcatccag cattgcgtcc acacagtcaa cagtagagtt tgataaaatat    5160 atttaatgag tgcctactat atgcatctgg gtcatgagat agtgatccta ttctcaagga    5220
gcataaattt gaacattgta cgaactaggt gatatttgtt actagagttt tgtttgaacg    5280
ttttattctc tcataaacat ttatttaata cctgcagtga tgaagttact ctgccatgta    5340
ttgggatgga ttccaaagtg agtaagagat agtttctgct tttccattgc ttgtaaataa    5400
acaaggtaga tgggtaggca ttataatgca atgaaagcag attatgatat gtagcatcag    5460
acaactgtaa acagaatgta acaggagttc tgaagaggag atcatgtcca gccgagttga    5520
ccaggacaag tgactttttaa gtttggccta gattgagata gaaataaatg gaattttat    5580 gataagatta tgtgactata ctacatacca ggtatattga cttggagaat aatattaatg    5640
agtgattgca aagcatgtat cttgaagttc ttgtctacat ttgcctttt cttcccttac    5700 gttatttact acagaaattt taaaatgca atctactacc ttaacataaa ttaatacatc    5760
ttagaagtaa tgataaaatt aaatttacta taatcattat tggctgatac ttgaattgcc    5820
cttggaacga gttaaaggta tcataaactt tctgggctgg gcacggtgct cacgcctgta    5880
atcccagcac tttgggaggc cgaggcgggc ggatcacgag gtcaggagat cgagaccacg    5940
gtgaaacccg gtctctacta aaaatacaaa aaattagctg gcgcagtgg cgggcgcctg    6000 tagtcccagc tactcgggag gctgaggcag gagaatggcg tgaacccggg aggcggagct    6060
tgcagtgagc cgagatggcg ccacagcact ccagcctggg cgacagagcg agactccgtc    6120
tcaaaaaaaa aaaaaaaaaa aagatatcat aaacttcctt aggagattaa taaggtcacg    6180
ggagctgatt gtaatattta gtttccctct gaatagatta atttaaagta gtcatgtaat    6240
gttttttggg ttgcttacaa atgtctttt attccaagca ggactataat atggatttag    6300
agctcgacga gtattataac aagacacttg ccacagaaa taatactgct gccactcgga    6360
attctgattt cccagtctgg gatgactata aaagcagtgt agatgactta cagtattttc    6420
tgattgggct ctatacattt gtaagtcttc ttggctttat ggggaatcta cttatttaa    6480 tggctctcat gaaaagcgt aatcagaaga ctacggtaaa cttcctcata ggcaatctgg    6540 cctttctga tatcttggtt gtgctgtttt gctcacctt cacactgacg tctgtcttgc    6600
tggatcagtg gatgtttggc aaagtcatgt gccatattat gcctttctt caatgtgtgt    6660 cagttttggt ttcaacttta attttaatat caattgccat tgtcaggtat catatgataa    6720
aacatcccat atctaataat ttaacagcaa accatggcta ctttctgata gctactgtct    6780
```

```
ggacactagg ttttgccatc tgttctcccc ttccagtgtt tcacagtctt gtggaacttc    6840
aagaaacatt tggttcagca ttgctgagca gcaggtattt atgtgttgag tcatggccat    6900
ctgattcata cagaattgcc tttactatct ctttattgct agttcagtat attctgccct    6960
tagtttgtct tactgtaagt catacaagtg tctgcagaag tataagctgt ggattgtcca    7020
acaaagaaaa cagacttgaa gaaaatgaga tgatcaactt aactcttcat ccatccaaaa    7080
agagtgggcc tcaggtgaaa ctctctggca gccataaatg gagttattca ttcatcaaaa    7140
aacacagaag aagatatagc aagaagacag catgtgtgtt acctgctcca gaaagacctt    7200
ctcaagagaa ccactccaga atacttccag aaaactttgg ctctgtaaga agtcagctct    7260
cttcatccag taagttcata ccaggggtcc ccacttgctt tgagataaaa cctgaagaaa    7320
attcagatgt tcatgaattg agagtaaaac gttctgttac aagaataaaa aagagatctc    7380
gaagtgtttt ctacagactg accatactga tattagtatt tgctgttagt tggatgccac    7440
tacacctttt ccatgtggta actgatttta atgacaatct tatttcaaat aggcatttca    7500
agttggtgta ttgcatttgt catttgttgg gcatgatgtc ctgttgtctt aatccaattc    7560
tatatgggtt tcttaataat gggattaaag ctgatttagt gtcccttata cactgtcttc    7620
atatgtaata attctcactg tttaccaagg aaagaacaaa tgctggggtc atataaaata    7680
tatttatgat aactatttac atataataaa tagaaatttt gttaacatgg aatttaattt    7740
atgtgaaaga gttctggatt caaatgtcag ttcataatat atggaagata attttatgtg    7800
ttatagtagg attaatttat ttagttgtgc agtcagtgtc aatccaatct gtaatttcac    7860
tttagaaggt tgtattacct tccacttcca tgttgtctta taaacaaatg aattgtattt    7920
tttgttgaaa gtaaaagtta tatctaacca actcagtact tttgtccaaa aatataataa    7980
gaaaaaattt ttctcgagga acttttaatt tcaaacttga agaatatcta ccagctatct    8040
atatcatttc tactccatag gcttcttaat gtttagtttg tgaagtacag aaaaaattta    8100
atatgcctgg aaaatcacaa ctaaatgaca gatgtatgcc caaattatga ttataatctt    8160
caacattaac tacagttttg gaagtcctgt aggaaaatgc tattgcctat tgagaattgg    8220
tcaaattgtc aatttaactc cactgtccta gtaatacaca gtaatttac caaataaaga     8280 attttaaatc ctttccagac tcattataca acattaaaca ctaccaataa aagttgtttt    8340
catatacatc aaaactattc taaaatgtga a                                   8371
```

<210> SEQ ID NO 2
<211> LENGTH: 445
<212> TYPE: PRT
<213> ORGANISM: Homo sapiens

<400> SEQUENCE: 2

```
Met Asp Leu Glu Leu Asp Glu Tyr Tyr Asn Lys Thr Leu Ala Thr Glu
 1               5                  10                  15

Asn Asn Thr Ala Ala Thr Arg Asn Ser Asp Phe Pro Val Trp Asp Asp
            20                  25                  30

Tyr Lys Ser Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Leu Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
```

```
                        85                  90                  95
Phe Thr Leu Thr Ser Val Leu Leu Asp Gln Trp Met Phe Gly Lys Val
                100                 105                 110
Met Cys His Ile Met Pro Phe Leu Gln Cys Val Ser Val Leu Val Ser
            115                 120                 125
Thr Leu Ile Leu Ile Ser Ile Ala Ile Val Arg Tyr His Met Ile Lys
        130                 135                 140
His Pro Ile Ser Asn Asn Leu Thr Ala Asn His Gly Tyr Phe Leu Ile
145                 150                 155                 160
Ala Thr Val Trp Thr Leu Gly Phe Ala Ile Cys Ser Pro Leu Pro Val
                165                 170                 175
Phe His Ser Leu Val Glu Leu Gln Glu Thr Phe Gly Ser Ala Leu Leu
            180                 185                 190
Ser Ser Arg Tyr Leu Cys Val Glu Ser Trp Pro Ser Asp Ser Tyr Arg
        195                 200                 205
Ile Ala Phe Thr Ile Ser Leu Leu Leu Val Gln Tyr Ile Leu Pro Leu
210                 215                 220
Val Cys Leu Thr Val Ser His Thr Ser Val Cys Arg Ser Ile Ser Cys
225                 230                 235                 240
Gly Leu Ser Asn Lys Glu Asn Arg Leu Glu Glu Asn Glu Met Ile Asn
                245                 250                 255
Leu Thr Leu His Pro Ser Lys Lys Ser Gly Pro Gln Val Lys Leu Ser
            260                 265                 270
Gly Ser His Lys Trp Ser Tyr Ser Phe Ile Lys Lys His Arg Arg Arg
        275                 280                 285
Tyr Ser Lys Lys Thr Ala Cys Val Leu Pro Ala Pro Glu Arg Pro Ser
    290                 295                 300
Gln Glu Asn His Ser Arg Ile Leu Pro Glu Asn Phe Gly Ser Val Arg
305                 310                 315                 320
Ser Gln Leu Ser Ser Ser Ser Lys Phe Ile Pro Gly Val Pro Thr Cys
                325                 330                 335
Phe Glu Ile Lys Pro Glu Glu Asn Ser Asp Val His Glu Leu Arg Val
            340                 345                 350
Lys Arg Ser Val Thr Arg Ile Lys Lys Arg Ser Arg Ser Val Phe Tyr
        355                 360                 365
Arg Leu Thr Ile Leu Ile Leu Val Phe Ala Val Ser Trp Met Pro Leu
    370                 375                 380
His Leu Phe His Val Val Thr Asp Phe Asn Asp Asn Leu Ile Ser Asn
385                 390                 395                 400
Arg His Phe Lys Leu Val Tyr Cys Ile Cys His Leu Leu Gly Met Met
                405                 410                 415
Ser Cys Cys Leu Asn Pro Ile Leu Tyr Gly Phe Leu Asn Asn Gly Ile
            420                 425                 430
Lys Ala Asp Leu Val Ser Leu Ile His Cys Leu His Met
        435                 440                 445

<210> SEQ ID NO 3
<211> LENGTH: 2143
<212> TYPE: DNA
<213> ORGANISM: Homo sapiens

<400> SEQUENCE: 3
agctcgtcga cctgacctgc cacaaagtta gaagaaagga ttgattcaag aaagactata    60
atatggattt agagctcgac gagtattata acaagacact tgccacagag aataatactg   120
```

```
ctgccactcg gaattctgat ttcccagtct gggatgacta taaaagcagt gtagatgact    180
tacagtattt tctgattggg gtctatacat ttgtaagtct tcttggcttt atggggaatc    240
tacttatttt aatggctctc atgaaaaagc gtaatcagaa gactacggta aacttcctca    300
taggcaatct ggccttttct gatatcttgg ttgtgctgtt ttgctgacct tcacactga     360
cgtctgtctt gctggatcag tggatgtttg gcaaagtcat gtgccatatt atgcctttc    420
ttcaatgtgt gtcagttttg gtttcaactt taattttaat atcaattgcc attgtcaggt    480
atcatatgat aaaacatccc atatctaata atttaacagc aaaccatggc tacttttctga   540
tagctactgt ctggacacta ggttttgcca tctgttctcc ccttccagtg tttcacagtc    600
ttgtggaact tcaagaaaca tttggttcag cattgctgag cagcaggtat ttatgtgttg    660
agtcatggcc atctgattca tagagaattg cctttactat ctctttattg ctagttcagt    720
atattctgcc cttagtttgt cttactgtaa gtcatacaag tgtctgcaga agtataagct    780
gtggattgtc caacaaagaa aacagacttg aagaaaatga gatgatcaac ttaactcttc    840
atccatccaa aaagagtggg cctcaggtga aactctctgg cagccataaa tggagttatt    900
cattcatcaa aaaacacaga agaagatata gcaagaagac agcatgtgtg ttacctgctc    960
cagaaagacc ttctcaagag aaccactcca gaatacttcc agaaaacttt ggctctgtaa   1020
gaagtcagct ctcttcatcc agtaagttca taccaggggt ccccacttgc tttgagataa   1080
aacctgaaga aaattcagat gttcatgaat tgagagtaaa acgttctgtt acaagaataa   1140
aaaagagatc tcgaagtgtt ttctacagac tgaccatact gatattagta tttgctgtta   1200
gttggatgcc actacacctt ttccatgtgg taactgattt taatgacaat cttatttcaa   1260
ataggcattt caagttggtg tattgcattt gtcatttgtt gggcatgatg tcctgttgtc   1320
ttaatccaat tctatatggg tttcttaata atgggattaa agctgattta gtgtcccttta   1380
tacactgtct tcatatgtaa taattctcac tgtttaccaa ggaaagaaca aatgctgggg   1440
tcatataaaa tatatttatg ataactattt acatataata aatagaaatt ttgttaacat    1500
ggaatttaat ttatgtgaaa gagttctgga ttcaaatgtc agttcataat atatggaaga    1560
taattttatg tgttatagta ggattaattt atttagttgt gcagtcagtg tcaatccaat    1620
ctgtaattc actttagaag gttgtattac cttccacttc catgttgtct tataaacaaa    1680
tgaattgtat ttttgttga agtaaaagt tatatctaac caactcagta cttttgtcca     1740
aaaatataat aagaaaaat ttttctcgag gaacttttaa tttcaaactt gaagaatatc    1800
taccagctat ctatatcatt tctactccat aggcttctta atgtttagtt tgtgaagtac    1860
agaaaaaatt taatatgcct ggaaaatcac aactaaatga cagatgtatg cccaaattat    1920
gattataatc ttcaacatta actacagttt tggaagtcct gtaggaaaat gctattgcct    1980
attgagaatt ggtcaaattg tcaatttaac tccactgtcc tagtaataca caagtaattt    2040
accaaataaa gaattttaaa tcctttccag actcattata caacattaaa cactaccaat    2100
aaaagttgtt ttcatataca tcaaaactat tctaaaatgt gaa                     2143
```

<210> SEQ ID NO 4
<211> LENGTH: 445
<212> TYPE: PRT
<213> ORGANISM: Homo sapiens

<400> SEQUENCE: 4

Met Asp Leu Glu Leu Asp Asx Tyr Tyr Asn Lys Thr Leu Ala Thr Glu
1               5                   10                  15

-continued

```
Asn Asn Thr Ala Ala Thr Arg Asn Ser Asp Phe Pro Val Trp Asp Asp
                20                  25                  30

Tyr Lys Ser Ser Val Asp Asp Leu Gln Tyr Phe Leu Ile Gly Leu Tyr
            35                  40                  45

Thr Phe Val Ser Leu Leu Gly Phe Met Gly Asn Leu Leu Ile Leu Met
        50                  55                  60

Ala Leu Met Lys Lys Arg Asn Gln Lys Thr Thr Val Asn Phe Leu Ile
 65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Val
                100                 105                 110

Met Cys His Ile Met Pro Phe Leu Gln Cys Val Ser Val Leu Val Ser
            115                 120                 125

Thr Leu Ile Leu Ile Ser Ile Ala Ile Val Arg Tyr His Met Ile Lys
        130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
                180                 185                 190

Ser Ser Arg Tyr Leu Cys Val Glu Ser Trp Pro Ser Asp Ser Tyr Arg
            195                 200                 205

Ile Ala Phe Thr Ile Ser Leu Leu Leu Val Gln Tyr Ile Leu Pro Leu
        210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Lys Lys Ser Gly Pro Gln Val Lys Leu Ser
                260                 265                 270

Gly Ser His Lys Trp Ser Tyr Ser Phe Ile Lys Lys His Arg Arg Arg
            275                 280                 285

Tyr Ser Lys Lys Thr Ala Cys Val Leu Pro Ala Pro Glu Arg Pro Ser
        290                 295                 300

Gln Glu Asn His Ser Arg Ile Leu Pro Glu Asn Phe Gly Ser Val Arg
305                 310                 315                 320

Ser Gln Leu Ser Ser Ser Lys Phe Ile Pro Gly Val Pro Thr Cys
                325                 330                 335

Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
        355                 360                 365

Arg Leu Thr Ile Leu Ile Leu Val Phe Ala Val Ser Trp Met Pro Leu
    370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
            420                 425                 430
```

Lys Ala Asp Leu Val Ser Leu Ile His Cys Leu His Met
    435                 440                 445

<210> SEQ ID NO 5
<211> LENGTH: 2286
<212> TYPE: DNA
<213> ORGANISM: Rattus rattus

<400> SEQUENCE: 5

| | | | | | |
|---|---|---|---|---|---|
| gaattcggca | cgaggggttt | gcaaggtggc | ttggaagtca | actgccagta | ggaaatagcc | 60 |
| atccacacac | ctgagttcca | aggggggaaga | aagagattct | tatctgattc | tagtatggag | 120 |
| tttaagcttg | aggagcattt | taacaagaca | tttgtcacag | agaacaatac | agctgctgct | 180 |
| cggaatgcag | ccttccctgc | ctgggaggac | tacagaggca | gcgtagacga | tttacaatac | 240 |
| tttctgattg | ggctctatac | attcgtaagt | cttcttggct | tatgggcaa | tctacttatt | 300 |
| ttaatggctg | ttatgaaaaa | gcgcaatcag | aagactacag | tgaactttct | cataggcaac | 360 |
| ctggccttct | ccgacatctt | ggtcgtcctg | ttttgctccc | ctttcaccct | gacctctgtc | 420 |
| ttgttggatc | agtggatgtt | tggcaaaagc | atgtgccata | tcatgccgtt | ccttcaatgt | 480 |
| gtgtcagttc | tggtttcaac | tctgatttta | atatcaattg | ccattgtcag | gtatcatatg | 540 |
| ataaagcacc | ctatttctaa | caatttaacg | gcaaaccatg | gctacttcct | gatagctact | 600 |
| gtctggacac | tgggctttgc | catctgttct | cccctcccag | tgtttcacag | tcttgtggaa | 660 |
| cttaaggaga | ccttttgggct | cagcactgct | gagtagcaat | atctctgtgt | tgagtcatgg | 720 |
| ccctctgatt | catacagaat | tgctttcaca | atctctttat | tgctagtgca | gtatatcctg | 780 |
| cctctagtat | gtttaacggt | aagtcatacc | agcgtctgcc | gaagcataag | ctgtggattg | 840 |
| tcccacaaag | aaaacagact | cgaagaaaat | gagatgatca | acttaaccct | acagccatcc | 900 |
| aaaaagagca | ggaaccaggc | aaaaaccccc | agcactcaaa | agtggagcta | ctcattcatc | 960 |
| agaaagcaca | gaaggaggta | cagcaagaag | acggcctgtg | tcttacccgc | cccagcagga | 1020 |
| ccttcccagg | ggaagcacct | agccgttcca | gaaaatccag | cctccgtccg | tagccagctg | 1080 |
| tcgccatcca | gtaaggtcat | tccaggggtc | ccaatctgct | tgaggtgaa | acctgaagaa | 1140 |
| agctcagatg | ctcatgagat | gagagtcaag | cgttccatca | ctagaataaa | aaagagatct | 1200 |
| cgaagtgttt | tctacagact | gaccatactg | atactcgtgt | tcgccgttag | ctggatgcca | 1260 |
| ctccacgtct | tccacgtggt | gactgacttc | aatgataact | tgatttccaa | taggcatttc | 1320 |
| aagctggtat | actgcatctg | tcacttgtta | ggcatgatgt | cctgttgtct | aaatccgatc | 1380 |
| ctatatggtt | tccttaataa | tggtatcaaa | gcagacttga | gagcccttat | ccactgccta | 1440 |
| cacatgtcat | gattctctct | gtgcaccaaa | gagagaagaa | acgtggtaat | tgacacataa | 1500 |
| tttatacaga | agtattctgg | atctgaatgc | cagttcgtaa | tctacgtaag | atcatcttca | 1560 |
| tgttataata | tggttaattc | aatcagttgt | gcagagtcaa | tgtccatcta | atacaatttc | 1620 |
| atgtgttgaa | gtagtttaca | ttattttcca | ttttatgtca | ttggtaataa | gttgagtgat | 1680 |
| actctgtggt | ttagtgtaaa | atgtatgaag | tgacaagttg | tcccaaagag | catttaacta | 1740 |
| cagatttaag | gaatttctat | tatctgggta | tcttcatttc | tatttcacag | gcttcttaac | 1800 |
| attttttttgt | aaaagtacaa | aaatattcaa | aagtcagaac | tctattacag | atgtatgcat | 1860 |
| aaaagatgat | tataattttg | taggagaaag | atctgctcct | attagtgaag | attggtaaaa | 1920 |
| ttgtcagttt | aacccgtctg | tcctactact | aatatttaat | ttttcaaata | tgaaaaggtt | 1980 |
| tcagattttg | tttagattta | tatcacatta | aacactgtca | aataaaggct | gttttatat | 2040 |

```
gcatcgttga tgttccaaaa tgtgaagtct aaatggtgtc tgtatttcca attattaaat    2100
aacttctaag atcatttta aaagtctgta gatggtatgg atagctagtt gtttgttaat    2160
ataaagtaaa agtagatagc tgatttatgt tgtacctatg tcgtatgtat attaggagca    2220
gtttcagccc cacagaacac tctatcgtgt tgtctcacta aagtgaaagc aaacgaaaaa    2280
aaaaaa                                                               2286

<210> SEQ ID NO 6
<211> LENGTH: 445
<212> TYPE: PRT
<213> ORGANISM: Rattus rattus

<400> SEQUENCE: 6

Met Glu Phe Lys Leu Glu His Phe Asn Lys Thr Phe Val Thr Glu
 1               5                  10                  15

Asn Asn Thr Ala Ala Ala Arg Asn Ala Ala Phe Pro Ala Trp Glu Asp
            20                  25                  30

Tyr Arg Gly Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Val Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Ser
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Lys Glu Thr Phe Gly Ser Ala Leu Leu
            180                 185                 190

Ser Ser Lys Tyr Leu Cys Val Glu Ser Trp Pro Ser Asp Ser Tyr Arg
        195                 200                 205

Ile Ala Phe Thr Ile Ser Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser His Lys Glu Asn Arg Leu Glu Glu Asn Glu Met Ile Asn
                245                 250                 255

Leu Thr Leu Gln Pro Ser Lys Lys Ser Arg Asn Gln Ala Lys Thr Pro
            260                 265                 270

Ser Thr Gln Lys Trp Ser Tyr Ser Phe Ile Arg Lys His Arg Arg Arg
        275                 280                 285

Tyr Ser Lys Lys Thr Ala Cys Val Leu Pro Ala Pro Ala Gly Pro Ser
    290                 295                 300

Gln Gly Lys His Leu Ala Val Pro Glu Asn Pro Ala Ser Val Arg Ser
305                 310                 315                 320

Gln Leu Ser Pro Ser Ser Lys Val Ile Pro Gly Val Pro Ile Cys Phe
```

|  |  |  |  | 325 |  |  |  | 330 |  |  |  | 335 |  |
|---|---|---|---|---|---|---|---|---|---|---|---|---|---|
| Glu | Val | Lys | Pro | Glu | Ser | Ser | Asp | Ala | His | Glu | Met | Arg | Val | Lys |
|  |  |  | 340 |  |  |  | 345 |  |  |  | 350 |  |  |
| Arg | Ser | Ile | Thr | Arg | Ile | Lys | Lys | Arg | Ser | Arg | Ser | Val | Phe | Tyr | Arg |
|  |  | 355 |  |  |  |  | 360 |  |  |  |  | 365 |  |  |
| Leu | Thr | Ile | Leu | Ile | Leu | Val | Phe | Ala | Val | Ser | Trp | Met | Pro | Leu | His |
|  | 370 |  |  |  |  | 375 |  |  |  |  | 380 |  |  |  |
| Val | Phe | His | Val | Val | Thr | Asp | Phe | Asn | Asp | Asn | Leu | Ile | Ser | Asn | Arg |
| 385 |  |  |  |  | 390 |  |  |  |  | 395 |  |  |  |  | 400 |
| His | Phe | Lys | Leu | Val | Tyr | Cys | Ile | Cys | His | Leu | Leu | Gly | Met | Met | Ser |
|  |  |  |  | 405 |  |  |  |  | 410 |  |  |  |  | 415 |  |
| Cys | Cys | Leu | Asn | Pro | Ile | Leu | Tyr | Gly | Phe | Leu | Asn | Asn | Gly | Ile | Lys |
|  |  |  | 420 |  |  |  |  | 425 |  |  |  |  | 430 |  |  |
| Ala | Asp | Leu | Arg | Ala | Leu | Ile | His | Cys | Leu | His | Met | Ser |
|  |  |  | 435 |  |  |  |  | 440 |  |  |  | 445 |

<210> SEQ ID NO 7
<211> LENGTH: 1585
<212> TYPE: DNA
<213> ORGANISM: Mus musculus

<400> SEQUENCE: 7

```
gttattgtca tagcgtgcta ttgttcttca agctgctaat ggtcactgtc ttcttccaag      60
caggactcta gtatggaggt taaacttgaa gagcatttta caagacatt tgtcacggag      120
aacaatactg ctgccagtca gaacacggcc tcccctgcct gggaggacta cagaggcaca     180
gagaacaata cttctgctgc tcggaacact ccgtttccag tctgggagga ctatagaggc     240
agcgtagacg acttacaata cttcctgatt gggctctata catttgtaag tcttcttggt     300
tttatgggaa atctacttat cttaatggct gttatgaaaa agcgcaatca gaagactaca     360
gtgaactttc tcataggcaa cctggccttc tccgacattt tggttgtcct gttttgctcc     420
cctttcaccc tgacctctgt cttgttggat cagtggatgt tcggcaaagc catgtgccat     480
atcatgccat tccttcagtg tgtatcagtt ctggtttcaa ctctgatttt aatatcgatt     540
gccattgtca ggtatcatat gataaagcac cctatatcta acatttaac agcaaaccat      600
ggctacttcc tgatagcatc tgtctggaca ctgggctttg ccatctgttc tcccctccca     660
gtgtttcaca gccttgtgga acttaaggaa acctttggct cagcattgct aagcagcaag     720
tatttgtgtg ttgagtcatg gccctctgat tcatacagaa ttgctttcac aatctctta     780
ttgttagttc agtatatcct gcctctagta tgtttaacag taagtcatac tagtgtctgc     840
aggagtataa gctgtggatt gtcccacaaa gaaaacagac tcgaagaaaa tgagatgatc     900
aacttaactc tacatccatc caaaaagagt cgggaccagg caaaactccc cagcactcaa     960
aagtggagct actcattcat cagaaagcac cgaagaaggt acagcaagaa gacggcatgc     1020
gtgttacccg ccccagcagg accttcccag gagaagcacc taaccgttcc agaaaaccca    1080
ggctcggtcc gtagccagct gtcaccatcc agtaaggtta ttccagggt cccgatctgc      1140
tttgaggtga aacctgaaga aagctcagat gctcaggaga tgagagtcaa gcgttccctc    1200
acgagaataa agaagagatc tcgcagtgtt ttctacagac tgactatatt gatattagtg     1260
ttcgctgtta gctggatgcc actccacgtc ttccacgtgg tgaccgattt caatgataac    1320
ctgatttcca ataggcattt caagctggtg tactgcatct gtcacttgtt aggcatgatg    1380
tcctgttgtc ttaatccgat cttatatgga ttccttaata atggtatcaa agcagacttg    1440
```

-continued

```
agagcccttacccactgcctacacatgtcatgattctctctgtgcaccgaggagagaaga    1500 aatgtggagactgcccacaatacatctgtgctaattgatgcataatttacataaacgtgt    1560 ctggatctgaatgccagtttgtaat                                        1585
```

<210> SEQ ID NO 8
<211> LENGTH: 466
<212> TYPE: PRT
<213> ORGANISM: Mus musculus

<400> SEQUENCE: 8

```
Met Glu Val Lys Leu Glu His Phe Asn Lys Thr Phe Val Thr Glu
 1               5                  10                  15

Asn Asn Thr Ala Ala Ser Gln Asn Thr Ala Ser Pro Ala Trp Glu Asp
                20                  25                  30

Tyr Arg Gly Thr Glu Asn Asn Thr Ser Ala Ala Arg Asn Thr Pro Phe
            35                  40                  45

Pro Val Trp Glu Asp Tyr Arg Gly Ser Val Asp Asp Leu Gln Tyr Phe
        50                  55                  60

Leu Ile Gly Leu Tyr Thr Phe Val Ser Leu Leu Gly Phe Met Gly Asn
65                  70                  75                  80

Leu Leu Ile Leu Met Ala Val Met Lys Lys Arg Asn Gln Lys Thr Thr
                85                  90                  95

Val Asn Phe Leu Ile Gly Asn Leu Ala Phe Ser Asp Ile Leu Val Val
               100                 105                 110

Leu Phe Cys Ser Pro Phe Thr Leu Thr Ser Val Leu Leu Asp Gln Trp
           115                 120                 125

Met Phe Gly Lys Ala Met Cys His Ile Met Pro Phe Leu Gln Cys Val
       130                 135                 140

Ser Val Leu Val Ser Thr Leu Ile Leu Ile Ser Ile Ala Ile Val Arg
145                 150                 155                 160

Tyr His Met Ile Lys His Pro Ile Ser Asn Asn Leu Thr Ala Asn His
                165                 170                 175

Gly Tyr Phe Leu Ile Ala Ser Val Trp Thr Leu Gly Phe Ala Ile Cys
            180                 185                 190

Ser Pro Leu Pro Val Phe His Ser Leu Val Glu Leu Lys Glu Thr Phe
        195                 200                 205

Gly Ser Ala Leu Leu Ser Ser Lys Tyr Leu Cys Val Glu Ser Trp Pro
    210                 215                 220

Ser Asp Ser Tyr Arg Ile Ala Phe Thr Ile Ser Leu Leu Leu Val Gln
225                 230                 235                 240

Tyr Ile Leu Pro Leu Val Cys Leu Thr Val Ser His Thr Ser Val Cys
                245                 250                 255

Arg Ser Ile Ser Cys Gly Leu Ser His Lys Glu Asn Arg Leu Glu Glu
            260                 265                 270

Asn Glu Met Ile Asn Leu Thr Leu His Pro Ser Lys Lys Ser Arg Asp
        275                 280                 285

Gln Ala Lys Leu Pro Ser Thr Gln Lys Trp Ser Tyr Ser Phe Ile Arg
    290                 295                 300

Lys His Arg Arg Arg Tyr Ser Lys Thr Ala Cys Val Leu Pro Ala
305                 310                 315                 320

Pro Ala Gly Pro Ser Gln Glu Lys His Leu Thr Val Pro Glu Asn Pro
                325                 330                 335

Gly Ser Val Arg Ser Gln Leu Ser Pro Ser Lys Val Ile Pro Gly
            340                 345                 350
```

```
Val Pro Ile Cys Phe Glu Val Lys Pro Glu Glu Ser Ser Asp Ala Gln
        355                 360                 365

Glu Met Arg Val Lys Arg Ser Leu Thr Arg Ile Lys Lys Arg Ser Arg
    370                 375                 380

Ser Val Phe Tyr Arg Leu Thr Ile Leu Ile Leu Val Phe Ala Val Ser
385                 390                 395                 400

Trp Met Pro Leu His Val Phe His Val Val Thr Asp Phe Asn Asp Asn
                405                 410                 415

Leu Ile Ser Asn Arg His Phe Lys Leu Val Tyr Cys Ile Cys His Leu
            420                 425                 430

Leu Gly Met Met Ser Cys Cys Leu Asn Pro Ile Leu Tyr Gly Phe Leu
        435                 440                 445

Asn Asn Gly Ile Lys Ala Asp Leu Arg Ala Leu Ile His Cys Leu His
    450                 455                 460

Met Ser
465
```

NEUROPEPTIDE Y-Y5 RECEPTOR

The present invention relates to isolated DNA molecules which encode the neuropeptide Y-Y5 receptor. In addition the present invention relates to the use of these molecules in the production of the neuropeptide Y-Y5 receptor using recombinant technology and to methods of screening and testing compounds for neuropeptide Y (NPY) agonist or antagonist activity.

In developed affluent countries the prevalence of obesity is alarming and it is now a massive contribution to morbidity and mortality in addition to being socially disadvantageous. Fat deposition in the abdominal area is a particular problem in relation to risk of Type II diabetes and cardiovascular disease. However, until recently, the molecular mechanisms controlling appetite, energy expenditure and adiposity have been surprisingly ill-understood.

Obesity has well-known associations with non-insulin-dependent diabetes (NIDDM), hypertension, dyslipidaemia and coronary heart disease, as well as less obvious links with diseases such as osteoarthritis and various malignancies; it also causes considerable problems through reduced mobility and decreased quality of life. Seven forms of rodent obesities, determined by single gene mutations, have been identified: yellow [Ay], adipose [Ad], diabetes [db], fat [fat], tubby [tub] and obese [ob] in the mouse and fatty [fa] in the rat. The obese phenotypes caused by these mutations differ in their age of onset, severity and the degree of insulin resistance. Similar phenotypes can also be seen in obese humans. Recently the molecular bases for some of these mutations has been elucidated. Of these the [ob] gene product "leptin" has created the most interest. However, many other factors are also involved in regulating energy balance and body fat distribution. Four factors appear most likely to have an important role: these are neuropeptide Y (NPY), corticotropin releasing factor (CRF)/ACTH/ glucocorticoids, insulin and galanin. In particular, NPY and its receptors play an important role in the regulation of appetite and in a related manner, obesity.

Neuropeptide Y (NPY) forms a family (called the pancreatic polypeptide family) together with pancreatic polypeptide (PP) and peptide YY(PYY), which all consist of 36 amino acids and possess a common tertiary structure. Neuropeptide Y (NPY) receptors, members of the G protein-coupled receptor superfamily, are activated by one of the most abundant peptides in the mammalian nervous system and subsequently influence a diverse range of important physiological parameters, including effects on psychomotor activity, central endocrine secretion, anxiety, reproduction, vasoactive effects on the cardiovascular system and most importantly, potent effects on appetite. A number of neuropeptides and classical neurotransmitters, including noradrenaline and serotonin, modulate ingestive behaviours. However, NPY stands out from the many neurotransmitters with experimental effects on food intake in being able to induce obesity. Injections of NPY into the paraventricular nucleus (PVN), have been shown to increase, in a dose dependent manner, feeding and drinking behaviour in the rat. A single injection of NPY can increase food intake several-fold for several hours and is effective even during the light phase when rats usually eat little, and in animals that have already eaten to satiety. Consequently, NPY peptides are certainly among the most potent orexygenic substances known in either food deprived or satiated animals. Repeated NPY injections into the PVN result in a massive and persistent feeding response and the rats ultimately develop obesity, with a true increase in body fat content. The importance of NPY as a mediator of appetite/obesity regulation is further enhanced by the very recent report that the obese gene product leptin inhibits NPY synthesis and release.

Injections of NPY into the paraventricular nucleus cause a prompt and robust increase in plasma ACTH levels and there is clear evidence that NPY-induced ACTH secretion is mediated by corticotropin releasing factor (CRF). However, its mode of action as well as its interaction with CRF within the brain is largely unknown, as are its interrelationships with other hormones, such as insulin. Nevertheless an agent which increases appetite and raises glucocorticoid levels might be important in generating central obesity.

Specific agonists and antagonists of NPY are therefore likely to be of substantial benefit for therapy of a wide range of clinical disorders. As NPY possess a compact tertiary structure and different parts of the molecule are required for interaction with different subtypes of the receptor, the logical developments of both agonists and antagonists is critically dependent upon the availability and knowledge of specific receptor structure.

It is presently known that NPY binds specifically to at least five receptors; Y1, Y2, Y3, Y4 and Y1-like (or "atypical Y1"). While it has been demonstrated that NPY receptors couple to the adenylate cyclase second messenger system, it remains probable that additional NPY receptor subtypes exist since there is evidence that phosphatidylinositol turnover, cations, and arachidonic acid may also function as second messengers for NPY.

Since NPY agonists and antagonists may have commercial value as, for example, potential anti-hypertensive agents, cardiovascular drugs, neuronal growth factors, anti-psychotics, anti-obesity and anti-diabetic agents, the ability to produce NPY receptors by recombinant DNA technology would be advantageous. To this end, DNA molecules encoding Y1, Y2, Y3 and Y4 have previously been isolated.

The present inventors have now isolated novel DNA molecules encoding the human, mouse and rat Y1-like (hereinafter referred to as NPY-Y5) receptors. Similar DNA molecules encoding human and rat NPY-Y5 have been described in International (PCT) Patent Specification No. WO 96/16542, however, these encode receptors with, in the case of the human NPY-Y5, an additional 10 N-terminus amino acids, and, in the case of the rat 20 NPY-Y5, an additional 11 N-terminus amino acids. Through analysis of several cDNA clones and RT-PCR using specific primers for intron and exon sequences, the present inventors have confirmed that the human, mouse and rat NPY-Y5 receptor does not include these additional 10/11 amino acids. The DNA molecules described in WO 96/16542 may thus exhibit lower expression rates over those of the present invention. In addition, the receptors encoded by the DNA molecules described in WO 96/16542, may show lower and possibly altered activity.

Thus, in a first aspect, the present invention provides an isolated DNA molecule encoding an NPY-Y5 receptor having about 445 amino acids or a functionally equivalent fragment thereof.

Preferably, the isolated DNA molecule encodes an human, mouse or rat NPY-Y5 receptor.

Most preferably, the isolated DNA molecule has a nucleotide sequence substantially corresponding or, at least, >80% (more preferably, >95%) homologous to that shown:
  (i) at nucleotides 6291 to 7625 of FIG. 1 (SEQ ID NO:1),
  (ii) at nucleotides 63 to 1397 of FIG. 2 (SEQ ID NO:3),
  (iii) at nucleotides 115 to 1449 of FIG. 3 (SEQ ID NO:5), or (iv) at nucleotides 73 to 1470 of FIG. 4 (SEQ ID NO:7).

The isolated DNA molecule may be incorporated into plasmids or expression vectors, which may then be introduced into suitable bacterial, yeast and mammalian host cells. Such host cells may be used to express the NPY-Y5 receptor encoded by the isolated DNA molecule.

Accordingly, in a second aspect, the present invention provides a mammalian, yeast or bacterial host cell transformed with the DNA molecule of the first aspect.

In a third aspect, the present invention provides a method of producing NPY-Y5 receptors comprising culturing the host cell of the second aspect under conditions enabling the expression of the DNA molecule and optionally recovering the NPY-Y5 receptor.

Preferably, the host cell is mammalian or bacterial. Where the cell is mammalian, it is presently preferred that it be a Chinese hamster ovary (CHO) cell, human embryonic kidney 293 cell or insect Sf9 cells.

In a preferred embodiment, the NPY-Y5 receptor is expressed onto the surface of the host cell.

The DNA molecules of the present invention represent a NPY receptor which may be of interest both clinically and commercially as it is expressed in many regions of the body and NPY affects a wide number of systems.

By using the nucleic acid molecules of the present invention it is possible to obtain neuropeptide Y-Y5 receptor protein in a substantially pure form.

Accordingly, in a fourth aspect, the present invention provides NPY-Y5 receptor in a substantially pure form.

Preferably, the purified NPY-Y5 has an amino acid sequence substantially corresponding to any one of the amino acid sequences shown in FIG. 5.

In a fifth aspect, the present invention provides an antibody capable of specifically binding to an NPY-Y5 receptor.

In a sixth aspect, the present invention provides a non-human animal transformed with a DNA molecule according to the first aspect of the present invention.

In a seventh aspect, the present invention provides a method for detecting agonist or antagonist agents of NPY-Y5 receptor, comprising contacting a NPY-Y5 receptor or a cell transfected with and expressing the DNA molecule of the first aspect with a test agent under conditions enabling the activation of a NPY-Y5 receptor, and detecting an increase or decrease in NPY-Y5 receptor activity.

In a further aspect, the present invention provides a nucleic acid probe comprising a nucleotide sequence of 10 or more nucleotides capable of specifically hybridising to a unique sequence within the DNA molecule of the first aspect.

In a still further aspect, the present invention provides an antisense nucleic acid molecule comprising a nucleotide sequence capable of specifically hybridising to an mRNA molecule which encodes NPY-Y5 receptor so as to prevent translation of the mRNA molecule. Such antisense nucleic acid molecules may include a ribozyme region to catalytically inactivate mRNA to which it is hybridised.

The term "substantially corresponding" as used herein in relation to the nucleotide sequences shown in FIGS. 1 and 2 is intended to encompass minor variations in the nucleotide sequence which due to degeneracy in the DNA code do not result in a change in the encoded protein. Further, this term is intended to encompass other minor variations in the sequence which may be required to enhance expression in a particular system but in which the variations do not result in a decrease in biological activity of the encoded protein.

The term "substantially corresponding" as used herein in relation to amino acid sequences is intended to encompass minor variations in the amino acid sequences which do not result in a decrease in biological activity the NPY-Y5 receptor. These variations may include conservative amino Aid substitutions. The substitutions envisaged are:

G, A, V, I, L, M; D, E; N, Q; S, T; K, R, H; F, Y, W, H; and P, Nα-alkalamino acids.

The invention is hereinafter described by way of the following non-limiting example and further, with reference to the accompanying figures.

BRIEF DESCRIPTION OF THE FIGURES

FIG. 1 provides the nucleotide sequence (SEQ ID NO:1) of a genomic DNA molecule encoding the human NPY-Y5 receptor and includes the predicted amino acid sequence (SEQ ID NO:2).

FIG. 2 provides the nucleotide sequence (SEQ ID NO:3) of a EDNA encoding the human NPY-Y5 receptor and includes the predicted amino acid sequence (SEQ ID NO:4).

FIG. 3 provides the nucleotide sequence (SEQ ID NO:5) of a cDNA encoding the rat NPY-Y5 receptor and includes the predicted amino acid sequence (SEQ ID NO:6).

FIG. 4 provides the nucleotide sequence (SEQ ID NO:7) of a genomic DNA encoding the mouse NPY-Y5 receptor and includes the predicted amino acid sequence (SEQ ID NO:8).

FIG. 5 shows the degree of identity between the predicted amino acid sequence of the human (SEQ ID NOS:2 and 4), mouse (SEQ ID NO:6) and rat (SEQ ID NO:8) NPY-Y5 receptor proteins.

EXAMPLE

Figure 6A:
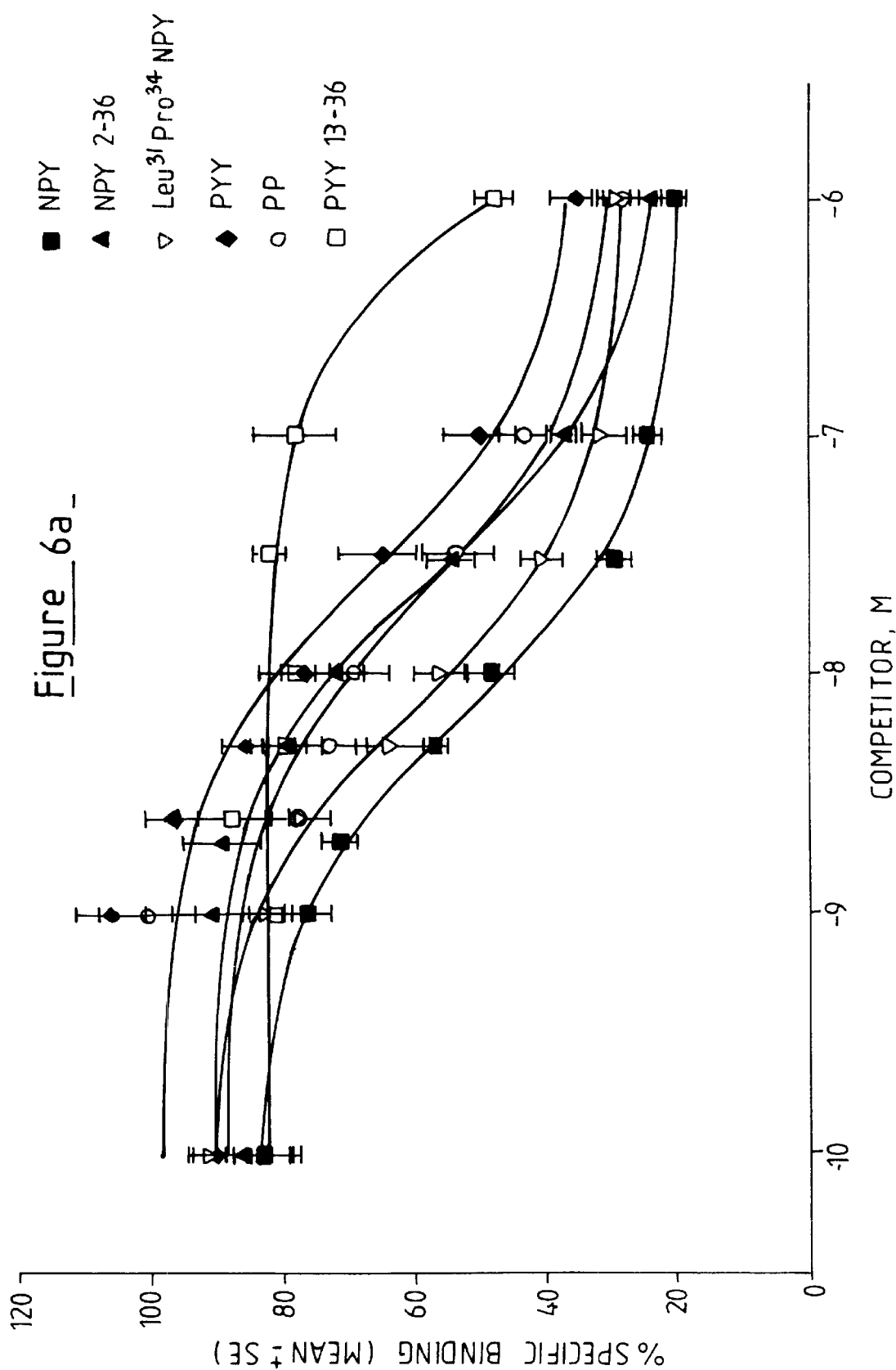
FIGS. 6a–f provide graphical results of binding assays conducted with CHO cells expressing NPY-Y5, Y5 ligands assayed were NPY, Leu 31 Pro 34 NPY, PP, PYY, NPY 2–36 and PYY 13–36.
Figure 6B:
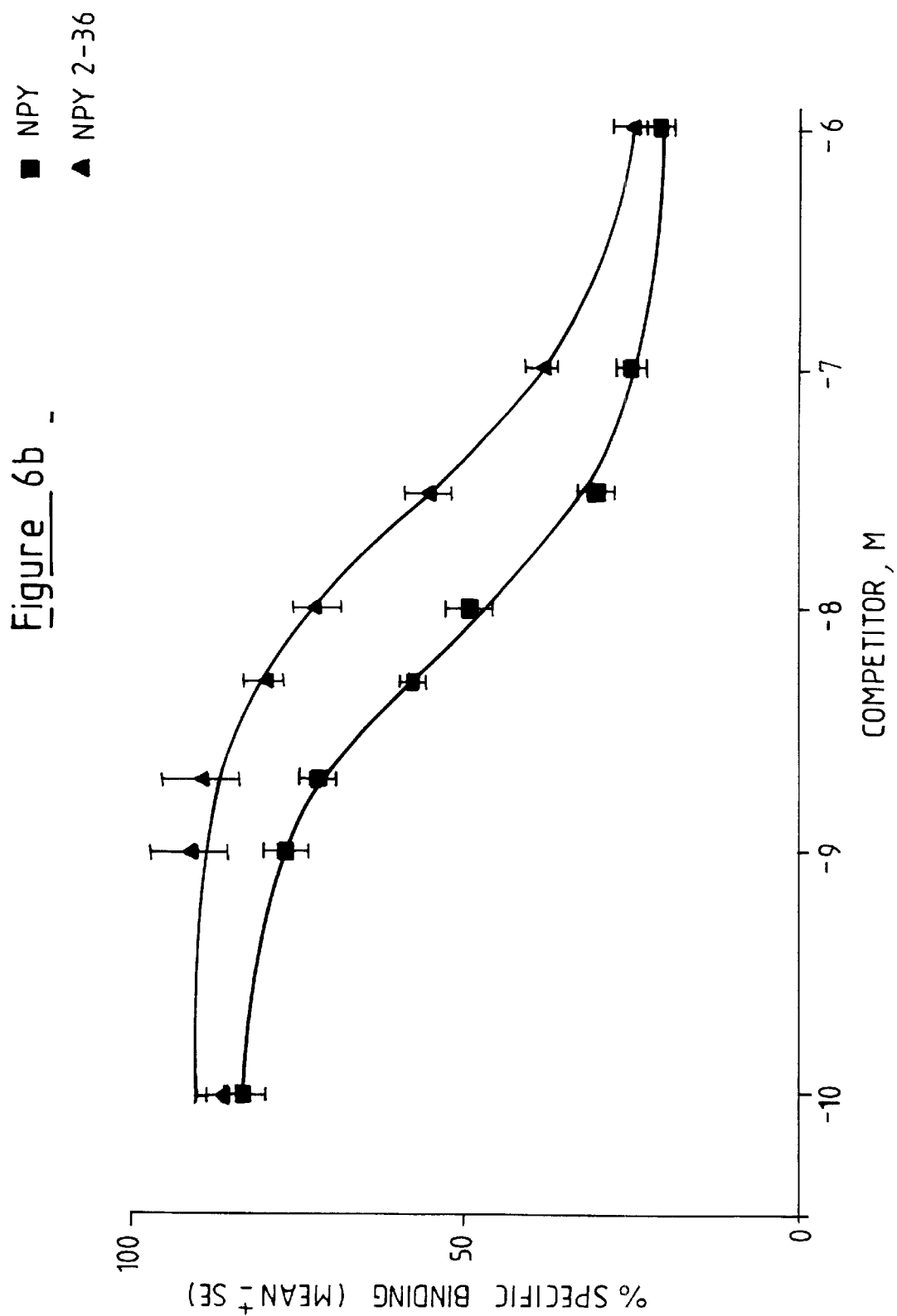
Figure 6C:
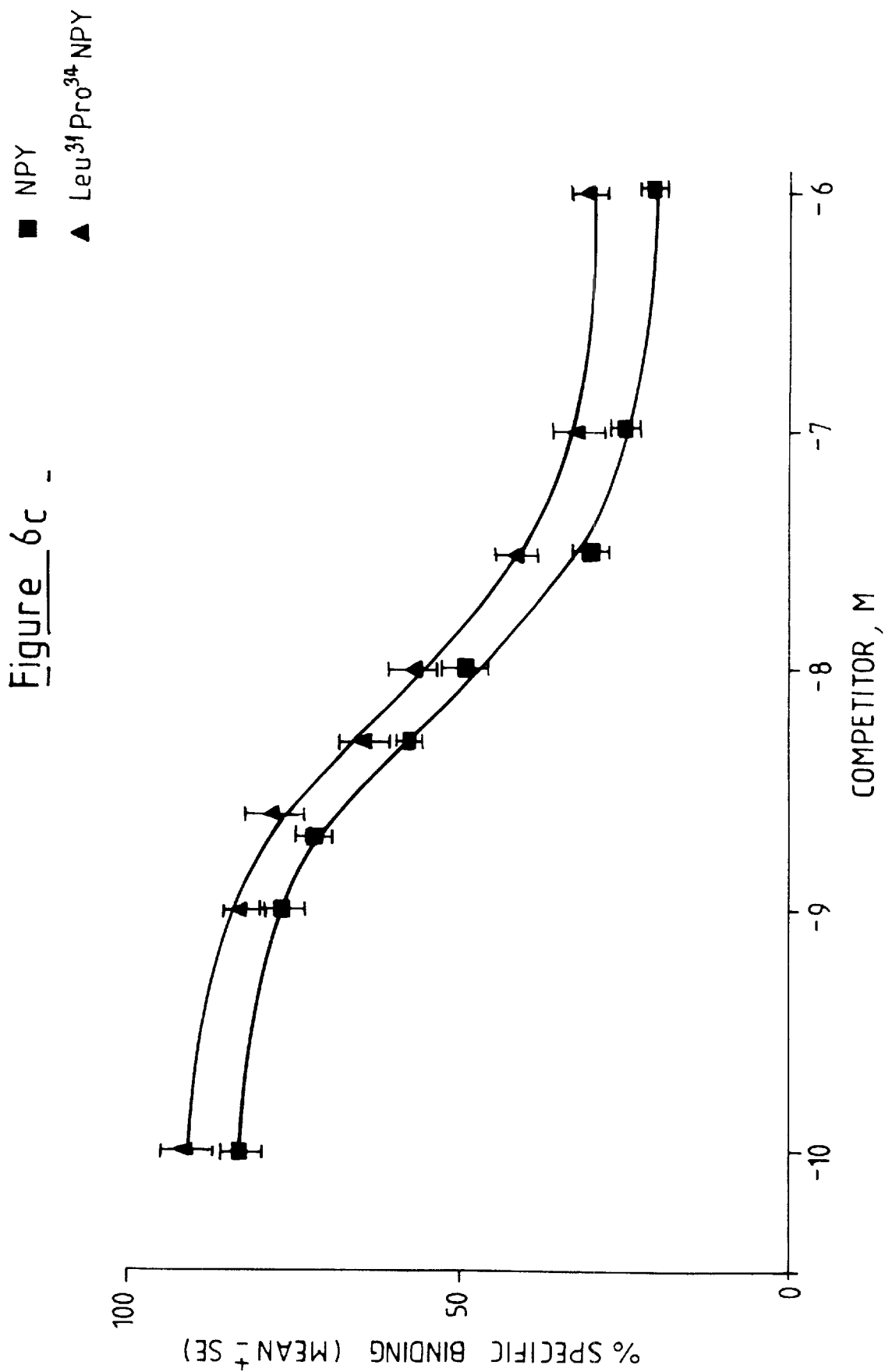
Figure 6D:
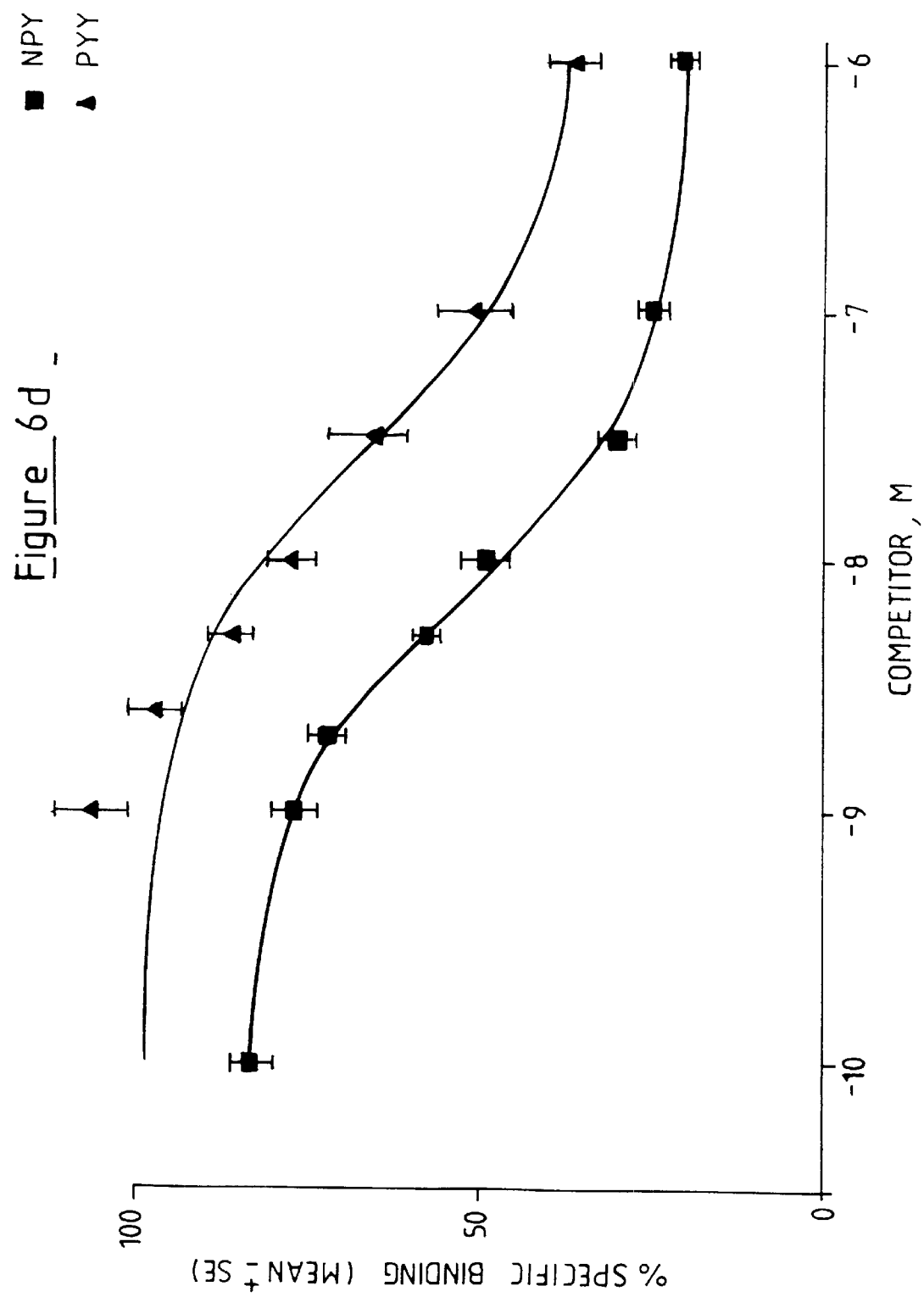
Figure 6E:
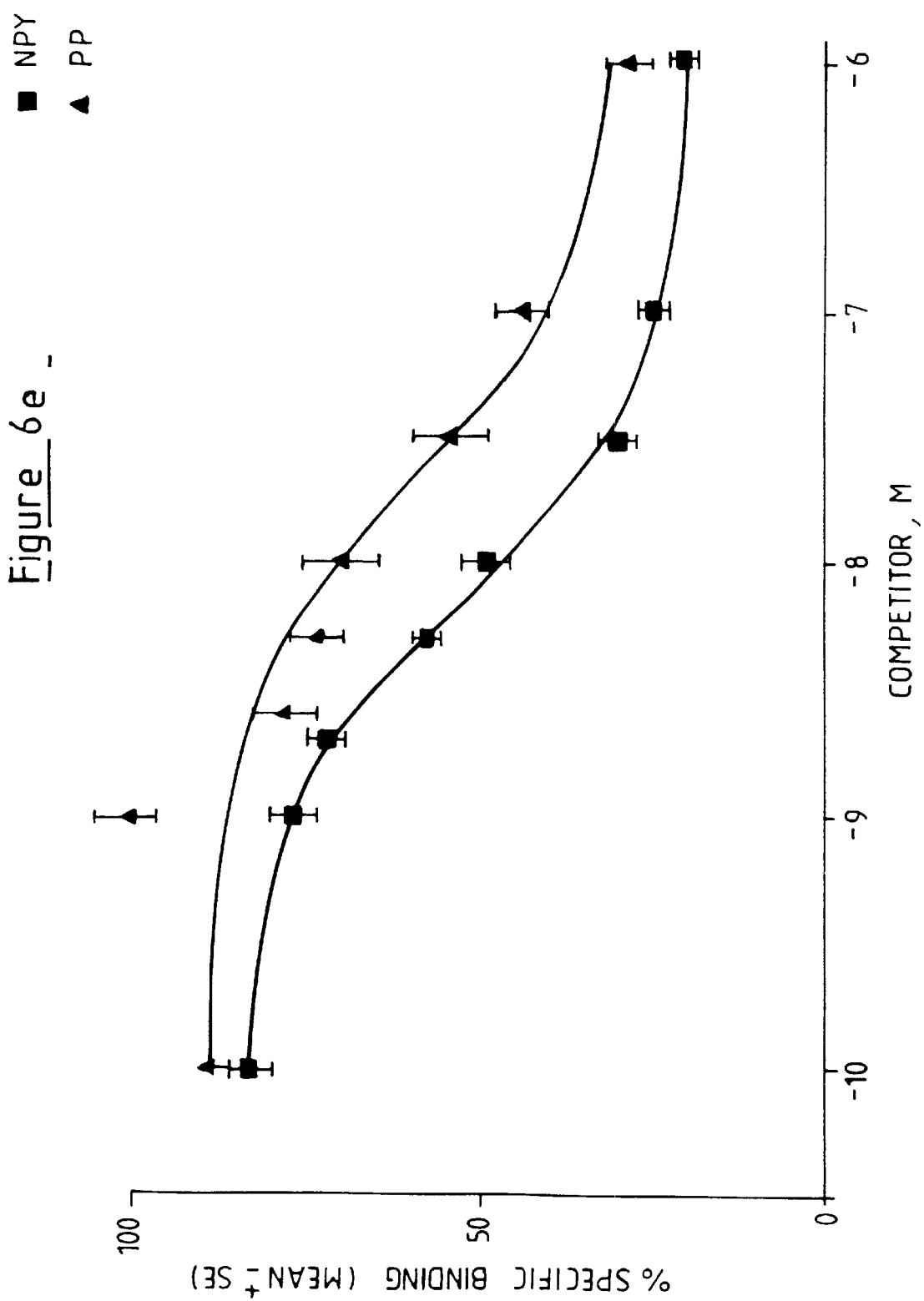
Figure 6F:
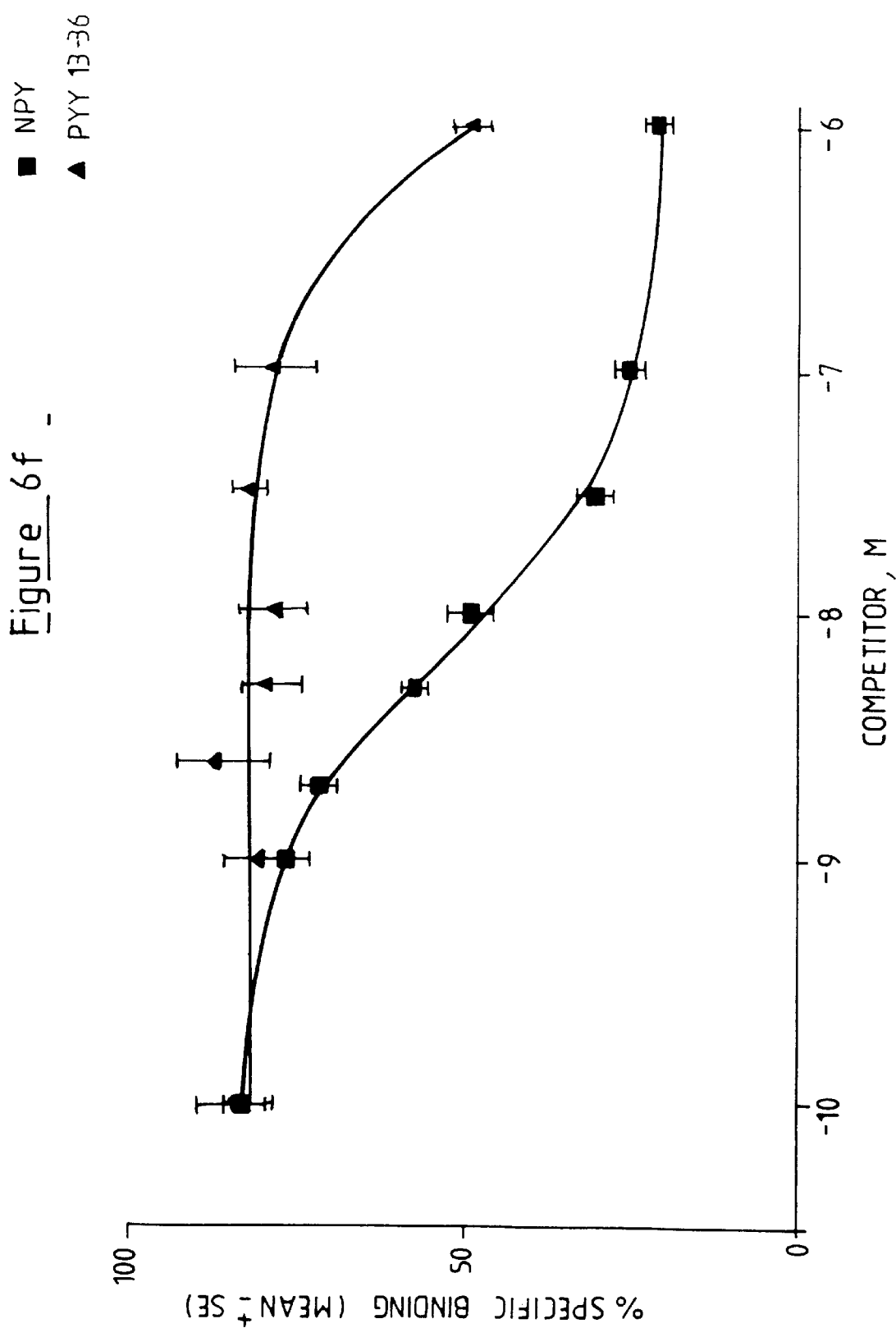

Experimental Procedures cDNA and Genomic Library Screening

A human genomic P1 DNA library (Genome-Systems), a human foetal brain cDNA library (P. Seeburg, University of Heidelberg) and a rat hypothalamic cDNA library (Stratagene) were screened with a 632 bp $^{32}$P-labelled EcoRI/Pst1 fragment flanking exon 1C of the human NPY-Y1 gene. Hybridisation with the probe was performed in a solution containing 6×SSC, 5×Denhardt's solution, 0.1% SDS and 100mg/ml denatured and sheared salmon sperm DNA at 60° C. for 16 h. Filters were washed twice for 15 min in 2×SSC/0.1% SDS at 60° C. followed by a 15 min wash in 0.1×SSC/0.1% SDS and exposed to X-ray film (Kodak, X-Omat) using an intensifying screen at −70° C. for 16h. P1 DNA from positive clones was isolated according to the manufacturer's protocol. The DNA was digested with EcoRI, HindIII, BamHI and PstI then subcloned into the Bluescript SK vector (Stratagene) generating clones covering all of the human Y1 and Y5 genes.

Nucleotide Sequence Determination

Supercoiled plasrnid DNA was alkaline-denatured and sequenced by the dideoxy chain termination method using T7 polymerase (Promega) (Sambrook et al., 1992). The oligonucleotide primers used initially were complementary to the flanking region of the vector and then based on sequences obtained in order to complete the sequence analysis.

Restriction Map Determination

P1 DNA was digested with restriction enzymes EcoRI, BamHI, HindIII, alone and in all possible combinations, electrophoresed on a 0.8% agarose gel, alkaline-denatured (0.4 M NaOH), capillary-transferred using 0.4 M NaOH to Hybond N$^+$ membranes and hybridised with several specific oligonucleotides, cDNAs and genoric DNA fragments obtained from the subcloning.

In Situ Hybridisation Analyses

Sense and antisense riboprobes to the human NPY-Y5 receptor were synthesised using the DIG RNA Labelling Kit (SP6/T7) (Boehringer Mannheim). cDNA corresponding to the coding region of the human NPY-Y5 receptor was linearised and transcribed with either T7 (for antisense riboprobe) or SP6 (for sense riboprobe) RNA polymerase according to the manufacturers instructions using digoxygenin labelled dUTP.

Postmortem brain tissue was obtained from a young adult male without neurological disease. Specific brain regions were dissected and fixed by immersion in formalin for 36 hours and then embedded in paraffin. 6 mm serial sections were collected on slides subbed in chrom alum and stored at 4° C. until used. Sections were dewaxed in Histoclear (National Diagnostics) for 5 min, rehydrated in 100%, 70% and 50% alcohol for 2 min each then washed in phosphate buffered saline (PBS) for 5 min.

Sections were pretreated for 10 min at room temperature with 5 mg/ml proteinase K (Boehringer Mannheim) in 5 mM Tris, pH 7.5, 5 mM EDTA. Sections were then washed twice with 0.1M glycine (in PBS) for 2 min, once in PBS then incubated for 1 h at room temperature in hybridisation buffer: 2×SSPE, 50% formamide, 5% dextran sulfate, 1×Denhardt's reagent, 100 mg/ml tRNA type X-SA (Sigma). Digoxigenin labelled riboprobes to sense and antisense DNA (500 ng) in 75ul of hybridisation buffer were added to the sections and hybridised at 42° C. for 18 h in a humidified environment using a Hybaid Omnislide PCR Thermal Cycler (Integrated Sciences). After hybridisation, sections were washed at room temperature in 2×saline sodium citrate (SSC) buffer, 0.15M NaCl/0.015 M Na-citrate, pH 7.0 for 10 min, then 0.2×SSC for 30 min followed by treatment with 20 mg/ml RNase [Sigma], in 10 mM Tris, pH 7.5, mM NaCl for 15 min at room temperature. After RNase treatment the slides were washed in 2×SSC for 5 min at room temperature then 0.2×SSC at 37° C. for 30 min.

Tissues were processed for immunological detection by washing for 10 min in buffer A (100 mM Tris-HCl, pH 7.5, 150 mM NaCl), then incubated for 30 min with a 2% blocking solution (Boehringer Mannheim) with 0.3% Triton X-100 in buffer A. The sections were then incubated for 2 hours with an alkaline phosphatase-conjugated anti-digoxigenin antiserum (Boehringer Mannheim, diluted 1/500 in buffer A plus 0.5% blocking reagent), washed twice for 5 min each in buffer A followed by a wash in 100 mM Tris-HCl, pH 9.5, 100 mM NaCl, 50 mM MgCl$_2$ for 2 min. The labelled probes were visualised using nitro blue tetrazolium and bromochloro-indoyl phosphate as substrates for 18 hours in the dark. Sections were washed for 10 min in 10 mM Tris-HCl, pH 8.0, 1 mM EDTA, then 3 quick washes in distilled water, mounted with Aquamount [Gurr] and examined using a Zeiss Axiophot microscope with Nomarsky optics using a blue filter.

Expression of NPY Y5

The rat Y5 receptor protein was expressed as follows: the mammalian expression construct rpHz17 was made by subcloning a 1.9 kb fragment containing the whole coding region and almost the entire 3'untranslated region of the rat NPY Y5 cDNA into the pPRC/CMV vector (Invitrogen). The construct is under the control of the CMV promoter and contains the neomycin gene for selection. The expression construct rpHz17 was transfected into mammalian cell lines CHO-K1 and HEK using a modified calcium phosphate transfection method.

NPY-Y5 Binding Assay

The coding region of the NPY-Y5 receptor was subcloned in the pRC/CMV expression vector and transfected into the chinese hamster ovary (CHO) K1 cell line by using a modified calcium phosphate transfection method. CHO cells were maintained under 5% $CO_2$ in Dulbecco's modified Eagles medium (DMEM)/Ham's F-12 medium (1:1) with 2 mM glutamine and 10% fetal calf serum. Stably transfected cells were selected with neomycin and tested for the ability to bind NPY/PYY analogues. Transfected cells (1×10$^6$) were incubated in 0.5 ml assay buffer [50 mM Tris-HCl, pH 7.4, 2 mM CaCl$_2$, 5 mM KCl, 120 mM NaCl, 1 mM MgCl$_2$, 0.1% bovine serum albumin] in the presence of 0.05nM $^{125}$I labeled NPY and increasing concentrations of human NPY and related peptides. Cells were incubated for 3 hours at 15° C. then layered onto 0.5 ml horse serum before being palleted in a microcentrifuge for 4 min. Radioactivity was measured for 1 min in a γ counter. Results of binding assays involving CHO cells expressing NPY-Y5 receptor are shown in Table 1, expressed as a percentage of the maximal specifically bound radiolabeled NPY. Results are the pooled data from three separate binding curves with triplicate points.

TABLE 1

| Peptide | IC$_{50}$ (nM) Mean +/− SE |
|---|---|
| NPY | 7.2 +/− 0.2 |
| Leu31 Pro34 NPY | 7.3 +/− 0.3 |
| PP | 21 +/− 4.3 |
| PYY | 25 +/− 4 |
| NPY 2–36 | 27 +/− 3.4 |
| PYY 13–36 | >1000 | cAMP Assays

CHO cells expressing NPY-Y5 receptor were grown and maintained in Dulbecco's modified Eagles medium: Hams F12 medium (1:1 v/v) supplemented with 2 mM L-glutamine and 10% (v/v) foetal calf serum at 37° C. under an atmosphere of 10% $CO_2$ in humidified air in 150 cm$^3$ flasks. Experiments were performed in 24 well cluster dishes when cells had reached confluence.

Inhibition of Forskolin-stimulated [$^3$H]-cAMP Accumulation

Cell monolayers were incubated for 2 h at 37° C. in 1 ml/well of HEPES buffered Hanks solution (HBH; 20 mM, pH 7.4) containing [$^3$H]-adenine (74 kBq/well). Prior to the addition of agonist, cells were incubated in 1 ml/well HBH containing the phosphodiesterase inhibitor Ro 20-1724 for 30 min. Agonists (in 10 μl HBH) were added to the assay system following the addition of forskolin (10 μM) and the incubation continued for 10 min. The temperature of the incubation medium was maintained at 37° C. during these manipulations. Incubations were terminated by the addition of 50 μl conc. HCl to each well which lysed the cells. [$^3$H]-cAMP content of the supernatant buffer from each well was isolated by sequential ion exclusion Dowex-alumina chromatography. After the addition of emulsifier scintillator (15 ml), radioactivity was determined by liquid scintillation counting. Results are provided in Table 2.

TABLE 2

| Peptide | IC$_{50}$ Values (n = 3) |
|---|---|
| NPY | 163.7 ± 70.0 nM |
| PYY | 45.1 ± 31.4 nM |
| PP | 73.4 ± 47.4 nM |
| [2–36]NPY | 242.5 ± 171.4 nM |
| Leu$^{31}$Pro$^{34}$NPY | 75.9 ± 38.3 nM |

Results

Identification of NPY-Y5 Receptor Gene

The cloning and characterisation of the 5' upstream region of the human NPY-Y1 receptor gene, while confirming the existence of several alternative 5' exons for the Y1 gene (Ball et al., 1995), also revealed a region of extensive homology with G-protein coupled receptors in exon 1C, involving a partial open reading frame in the opposite orientation. Comparison of this 200 amino acid sequence, which contained parts of the third intracellular loop and transmembrane domains VI and VII, with the Genbank database, identified the human NPY-Y1 receptor as the closest related receptor with 37% identity. Subcloning and sequencing of the entire 7 kb area between exon 1C and exon 1B of the Y1 gene confirmed the presence of a gene encoding a novel NPY receptor subtype named Y5 (FIG. 1). Screening of human fetal brain and rat hypothalamic cDNA libraries with a 632 bp human genomic Y5 fragment under high stringency identified full length cDNA clones for both species. These sequences encode a 445 amino acid long Y5 receptor (FIGS. 2 and 3). The human genomic sequence (FIG. 1) shows two candidate initiator ATG codons, however analysis of several cDNA clones and RT-PCR using specific primers for intron and exon sequences has established that one of these ATG codons (located 30 nucleotides upstream of the other ATG) is located within an intron. The overall identity between the human and rat NPY-Y5 receptors after this correction is 89%. FIG. 5 shows that the degree of identity between the predicted amino acid sequence of the human and rat NPY-Y5 receptors.

The exon which encodes the 5' untranslated region of the human Y5 gene is separated by a 2.7 kb intron from exon 2 and is located about 2.8 kb upstream of exon 1B of the NPY-Y1 gene. The close proximity of these two 5' exons orientated in opposite directions suggests a possible co-regulation of transcription of both genes through a common promoter region.

An interesting feature of the human Y5 gene, however, is the harbouring of exon iC of the NPY-Y1 gene within the coding region of the NPY-Y5 gene. The 100 bp long exon 1C encodes, in its opposite strand, a part of the Y5 sequence containing most of the third intracellular loop of the receptor protein. This cytoplasmic loop can vary significantly in size between G-protein coupled receptors and is thought to be involved in determination of the specificity of coupling to different G-protein complexes. In contrast to all other known NPY receptor subtypes, this region in the Y5 receptor is unusually large, consisting of about 150 amino acids. In the corresponding region of the NPY-Y1 gene, shortly after the fifth transmembrane domain, a small 97 bp intron containing an in frame stop codon interrupts the coding region (FIG. 1) suggesting that this noncoding region has gained two additional functions after duplication. One is to encode part of the Y5 protein sequence and the other is to fulfil a regulatory function in tissue specific transcription, as an alternatively spliced 5' exon of the Y1 gene. Transcription activation of exon 1C certainly will have an effect on Y5 expression, most likely inhibiting mRNA production. However, such a mechanism may represent only one aspect of a regulatory interaction between these two receptor genes. The close proximity of exon 1B of the Y1 gene and exon 1 of the Y5 gene suggests an additional control mechanism(s) for the specific transcriptional activation of one or the other gene.

Pharmacological Characterisation of the Y5 Receptor

Figure 7:
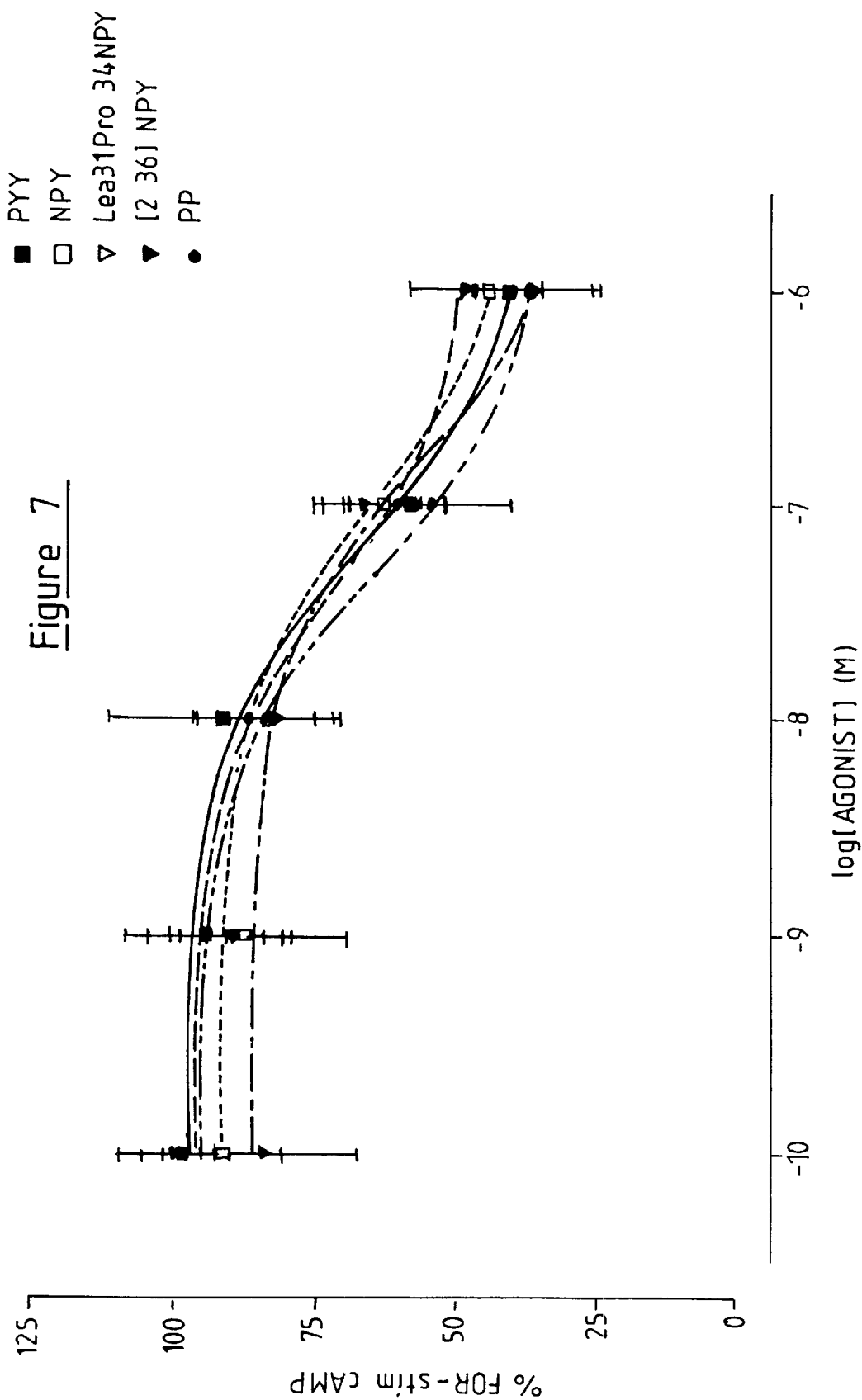
FIG. 7 provides graphical results of cAMP assays conducted on CHO cells expressing NPY-Y5 using the ligands NPY, Leu 31 Pro 34 NPY, PP, PYY and NPY 2–36.

NPY binding analysis of CHO cell lines stably expressing the rat Y5 receptor subtype show a ligand specificity and rank order of potency (NPY=NPY>PYY[Leu$^{31}$,Pro$^{34}$]= NPY[2–36]=PP>>PYY[13–36]) indicative of a NPY receptor with a Y1-like pharmacology, as well as responding strongly to the feeding specific ligand NPY[2–36] (FIGS. 6a–f). The same profile of selectivity for these different NPY analogues can be seen in the results obtained from experiments measuring the inhibition of adenylate cyclase activity (FIG. 7).

In situ Hybridisation Analysis

A comprehensive study was made of the distribution of the Y5 receptor mRNA in hypothalamic regions of the human hypothalamus. Hybridisation with a sense probe to Y5 showed no specific labelling, however, antisense probe showed extremely high expression of Y5 receptor mRNA is found in large neurons of the paraventricular nucleus. High levels are also found in the dorsomedial nucleus, supraoptic nucleus and in the mamillary body as well as in the midline thalamic nuclei. Within a nucleus the distribution was not always homogenous. For example in the dorsomedial region, clearly unlabelled large pyramidal neurons were found mingled with labelled neurons, suggesting functional specialisation. Preliminary results for the Y1 receptor suggest that the human NPY-Y1 receptor has a similar distribution to that of the Y5 receptor, however, with some identifiable differences supporting the theory of a co-regulatory transcription activation of the two genes.

Expression of NPY-Y5

The expressed Y5 receptor protein appears to have a unique distribution and relative affinities for different NPY/PYY/PP analogues. It is also expected that the Y5 receptor will be functionally unique, relative to other NPY receptors, and may be very important in, for example, the development of drugs for a number of conditions such as appetite/obesity disorders, hypertension, locomotor problems, memory loss, sleeping disorders, migraine and gastrointestinal (GI) and cardiovascular disorders.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Ball, H. J., Shine, J. & Herzog, H. (1995). Multiple promoters regulate tissue-specific expression of the human NPY-Y1 receptor gene. *J. Biol. Chem.* 270, 27272–27276.

2. Sambrook, J., Fritsch, E. F. & Maniatis, T. (1992). Molecule cloning (*A Laboratory Manual*) 2nd ed. (Cold Spring Harbor Laboratory Press, Cold Spring Harbor, N.Y.).

What is claimed is:

1. An isolated DNA molecule encoding an NPY-Y5 receptor consisting of about 445 amino acids, wherein said DNA molecule encodes a mammalian NPY-Y5 receptor.

2. An isolated DNA molecule according to claim 1, wherein said DNA molecule encodes a human, mouse or rat NPY-Y5 receptor.

3. An isolated DNA molecule according to claim 2, wherein the DNA molecule encodes a human NPY-Y5 receptor.

4. A method for detecting agonist or antagonist agents of NPY-Y5 receptor, comprising contacting a cell transformed with and expressing a DNA molecule according to claim 1 with a test agent under conditions enabling the activation of the NPY-Y5 receptor, and detecting an increase or decrease in the NPY-Y5 receptor activity.

5. An isolated DNA molecule encoding an NPY-Y5 receptor, wherein the DNA molecule is at least 95% identical to the nucleotide sequence shown:

(i) at nucleotides 6291 to 7625 of SEQ ID NO:1;

(ii) at nucleotides 63 to 1397 of SEQ ID NO:3;

(iii) at nucleotides 115 to 1449 of SEQ ID NO:5; or (iv) at nucleotides 73 to 1470 of SEQ ID NO:7.

6. An isolated DNA molecule encoding an NPY-Y5 receptor, wherein said DNA molecule comprises a nucleotide sequence selected from the group consisting of nucleotides 6291 to 7625 of SEQ ID NO:1, nucleotides 63 to 1397 of SEQ ID NO:3, nucleotides 115 to 1449 of SEQ ID NO:5, and nucleotides 73 to 1470 of SEQ ID NO:7.

7. The isolated DNA molecule encoding an NPY-Y5 receptor according to claim 6, wherein said DNA molecule comprises nucleotides 6291 to 7625 of SEQ ID NO:1.

8. The isolated DNA molecule encoding a NPY-Y5 receptor according to claim 6, wherein the DNA molecule comprises nucleotides 63 to 1397 of SEQ ID NO:3.

9. The isolated DNA molecule encoding a NPY-Y5 receptor according to claim 6, wherein the DNA molecule comprises nucleotides 115 to 1449 of SEQ ID NO:5.

10. The isolated DNA molecule encoding a NPY-Y5 receptor according to claim 6, wherein the DNA molecule comprises nucleotides 73 to 1470 of SEQ ID NO:7.

11. A plasmid or expression vector comprising a DNA molecule according to any one of claims 1 to 3 and 5 to 10.

12. A host cell transformed with a DNA molecule according to any one of claims 1 to 3 and 5 to 10.

13. A host cell according to claim 12, wherein the cell is a mammalian or bacterial cell.

14. A host cell according to claim 13, wherein the cell is a Chinese hamster ovary (CHO) cell or a human embryonic kidney (HEK) 293 cell.

15. A host cell according to claim 12, wherein the cell expresses NPY-Y5 receptor onto the cell's surface.

16. A host cell according to claim 12, wherein the cell is an insect Sf9 cell.

* * * * *